US011504497B2

(12) United States Patent
Jin et al.

(10) Patent No.: US 11,504,497 B2
(45) Date of Patent: Nov. 22, 2022

(54) SMART RELAXATION MASKS WITH WIRED EARPIECES

(71) Applicant: Bose Corporation, Framingham, MA (US)

(72) Inventors: Paul Jin, Waban, MA (US); Daniel K. Lee, Framingham, MA (US); Benjamin N. Davies, Northborough, MA (US); George E. P. Chute, Milford, MA (US)

(73) Assignee: Bose Corporation, Framingham, MA (US)

( * ) Notice: Subject to any disclaimer, the term of this patent is extended or adjusted under 35 U.S.C. 154(b) by 503 days.

(21) Appl. No.: 16/510,181

(22) Filed: Jul. 12, 2019

(65) Prior Publication Data

US 2021/0008331 A1 Jan. 14, 2021

(51) Int. Cl.
*A61M 21/02* (2006.01)
*A61N 5/06* (2006.01)
(Continued)

(52) U.S. Cl.
CPC ............. *A61M 21/02* (2013.01); *A61B 5/168* (2013.01); *A61N 5/0618* (2013.01);
(Continued)

(58) Field of Classification Search
CPC .......... A61M 21/02; A61M 2021/0044; A61M 2021/0022; A61M 2021/0027; A61M 2021/0083; A61M 2205/0216; A61M 2205/18; A61M 2205/332; A61M 2205/3375; A61M 2205/3584; A61M 2205/3592; A61M 2205/42; A61M 2205/507; A61M 2207/00; A61M 2230/04; A61M 2230/06; A61M 2230/10; A61M 2230/14; A61M 2230/42; A61M 2230/60; A61M 2230/63; A61M 2230/65; A61M 21/00; A61B 5/168; A61B 5/0205; A61B 5/4836; A61N 5/0618; A61N 2005/0648; A61N 2005/0651; H04R 1/1016;
(Continued)

(56) References Cited

U.S. PATENT DOCUMENTS 4,777,937 A * 10/1988 Rush ..................... A61M 21/00
600/27
5,599,274 A * 2/1997 Widjaja ................ A61M 21/00
600/26

(Continued)

FOREIGN PATENT DOCUMENTS

CA  2966774 A1  5/2016

OTHER PUBLICATIONS

Kidmose, Preben, Senior Member, IEEE; Looney, David, Member, IEE; Ungstrup, Michael, Member, IEEE; Rank, Mike Lind, Member, IEEE; Mandic, Danilo P, Fellow, IEEE,"A Study of Evoked Potentials From Ear-EEG", IEEE Transactions on Biomedical Engineering, vol. 60, No. 10, Oct. 2013, 7 pages.

(Continued)

*Primary Examiner* — Sunita Reddy
(74) *Attorney, Agent, or Firm* — Bose Corporation

(57) ABSTRACT

A relaxation mask includes: a main body that defines a pair of eye cavities; wiring; an earpiece that is coupled to the main body via the wiring; and a spring configured to bias the earpiece towards the main body.

9 Claims, 26 Drawing Sheets

(51) Int. Cl.
*H04R 1/10* (2006.01)
*A61B 5/16* (2006.01)
*A61M 21/00* (2006.01)
*A61B 5/0205* (2006.01)
*A61B 5/00* (2006.01)

(52) U.S. Cl.
CPC ......... *H04R 1/1016* (2013.01); *H04R 1/1075* (2013.01); *A61B 5/0205* (2013.01); *A61B 5/4836* (2013.01); *A61M 2021/0044* (2013.01); *A61N 2005/0648* (2013.01)

(58) Field of Classification Search
CPC .... H04R 1/1075; H04R 1/105; H04R 25/656; A61F 9/04
USPC ...................................................... 600/26–28
See application file for complete search history.

(56) References Cited

U.S. PATENT DOCUMENTS

| | | | |
|---|---|---|---|
| 8,249,287 B2 | 8/2012 | Silvestri et al. | |
| 8,852,073 B2 | 10/2014 | Genereux et al. | |
| 9,707,409 B2 | 7/2017 | Colbaugh | |
| 10,057,675 B2 | 8/2018 | Mankodi et al. | |
| 2004/0225340 A1 | 11/2004 | Evans | |
| 2008/0143954 A1* | 6/2008 | Abreu | G06F 3/167 |
| | | | 351/158 |
| 2009/0149721 A1 | 6/2009 | Yang | |
| 2011/0007929 A1 | 1/2011 | Rabu et al. | |
| 2011/0257713 A1 | 10/2011 | Clegg et al. | |
| 2012/0137406 A1 | 6/2012 | Hide | |
| 2014/0041091 A1* | 2/2014 | Sternlight | A61F 9/04 |
| | | | 2/12 |
| 2014/0303428 A1* | 10/2014 | Berka | A61B 5/6803 |
| | | | 600/27 |
| 2016/0005320 A1 | 1/2016 | deCharms et al. | |
| 2017/0189639 A1* | 7/2017 | Mastrianni | A61B 5/378 |
| 2017/0224951 A1* | 8/2017 | Weber | A61M 21/02 |
| 2018/0046432 A1* | 2/2018 | Derungs | G16H 10/60 |
| 2018/0110960 A1 | 4/2018 | Youngblood et al. | |
| 2018/0235540 A1 | 8/2018 | Kirszenblat et al. | |
| 2018/0295439 A1 | 10/2018 | Garrett | |

OTHER PUBLICATIONS

Goverdovsky, Valentin; von Rosenberg, Wilhelm; Nakamura, Takashi; Looney, David; Sharp, David J.; Papavassiliou, Christos; Morrell Mary J.; Mandic, Danilo P., "Hearables: Multimodal physiological in-ear sensing", published online: Jul. 31, 2017; from Scientific Reports, www.nature.com/scientificreports, 10 pages.

Looney, David; Kidmose, Preben; Park, Cheolsoo; Ungstrup, Michael; Rank, Mike Lind; Rosenkranz, Karin; Mandic, Danilo P., "The In-the-Ear Recording Concept", IEEE Pulse, Nov./Dec. 2012, 11 pages.

* cited by examiner

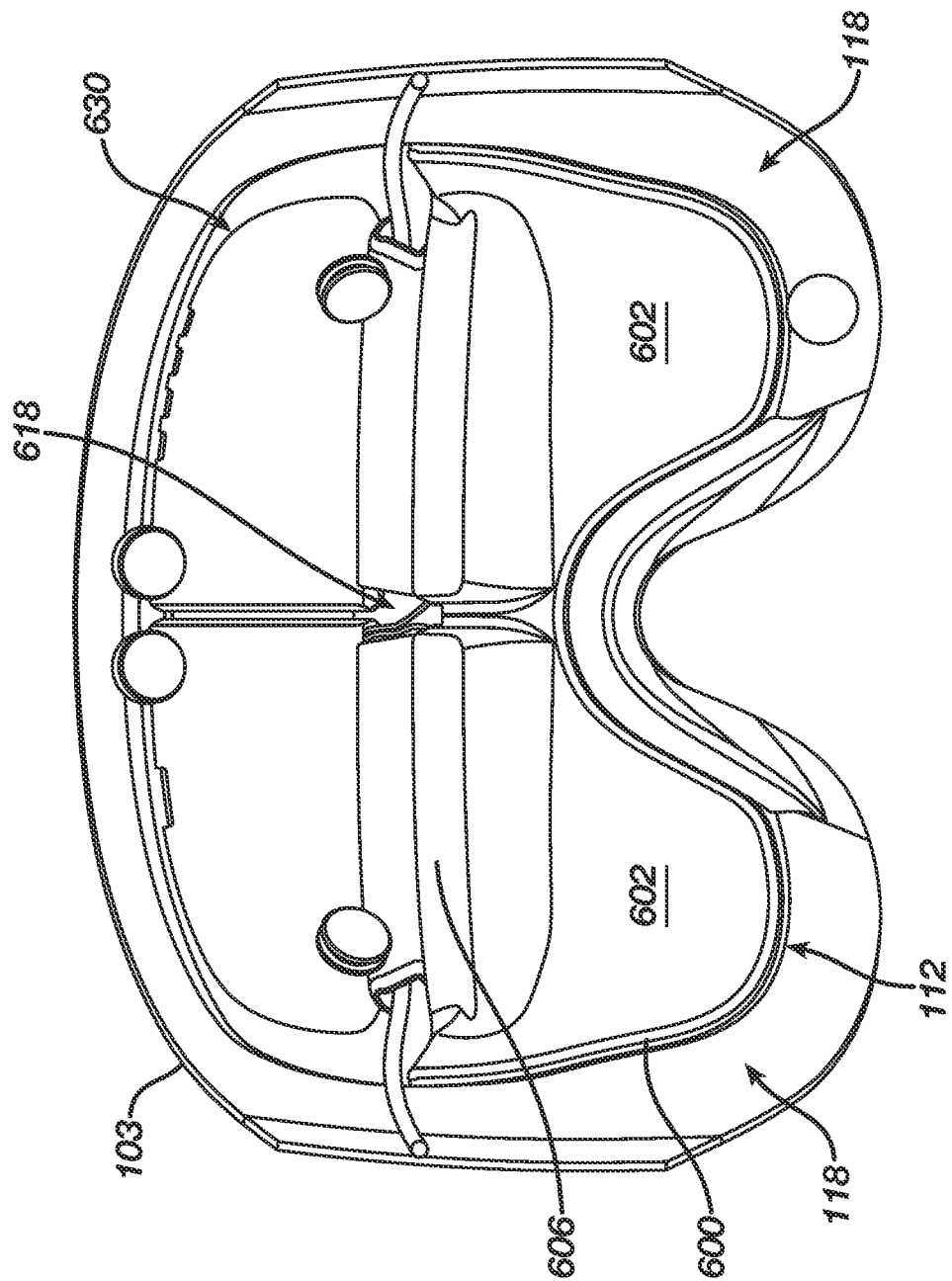

SMART RELAXATION MASKS WITH WIRED EARPIECES

FIELD

This disclosure relates to smart relaxation masks with wired earpieces. Aspects of the present disclosure relate to a smart relaxation mask configured to adjust an audio output of the smart relaxation mask provided via an earpiece(s). The adjusted output of the smart relaxation mask may help a subject achieve a state of relaxation and fall and stay asleep, and/or may assist a subject in gently awaking from sleep.

BACKGROUND

Most people have had the experience of their attention drifting away from daily tasks. For example, after some time of reading, working, commuting, interacting with others, or trying to fall asleep, a subject may experience emergence of thoughts unrelated to the task they are trying to perform. Such experiences are called mind wandering episodes. Some subjects try meditation to help increase focus or relax the mind; however, mind wandering still occurs despite purposeful efforts to avoid them.

Difficulty in falling and staying asleep negatively affects a subject's health. Stress and anxiety contribute to mind wandering episodes. Accordingly, stress and anxiety contribute to some challenges in falling and staying asleep. A need exists for assisting a subject to relax, fall asleep, and stay asleep without adversely affecting the subject's health in other, unintended ways.

SUMMARY

All examples and features mentioned herein can be combined in any technically possible manner.

In one aspect, a relaxation mask includes: a main body that defines a pair of eye cavities; wiring; an earpiece that is coupled to the main body via the wiring; and a spring configured to bias the earpiece towards the main body.

Implementations may include one of the following features, or any combination thereof.

In some implementations, the wiring defines the spring.

In certain implementations, the wiring includes a serpentine segment that defines the spring.

In some examples, the relaxation mask also includes an electronics enclosure and a light diffuser that is disposed within a first one of the cavities. A coupling member couples the light diffuser to the electronics enclosure. The coupling member defines a channel and the serpentine section is disposed within the channel.

In certain examples, the relaxation mask includes a sleeve that has a first open end and a second open end. The wiring passes through the sleeve and the sleeve is arranged to overlie a subject's temple region when the relaxation mask is worn.

In some cases, a high friction material is disposed on an inner surface of the sleeve and is arranged to inhibit movement of the wiring when the relaxation mask is worn.

In certain cases, the wiring includes a first round section arranged at the interface with the earpiece and the wiring includes a flat section that extends through the sleeve.

In some implementations, the relaxation mask includes an electronics enclosure that is supported by the main body. A first end of the wiring is coupled to the electronics enclosure and a second end of the wiring is coupled to the earpiece.

In certain implementations, the wiring includes a first round section arranged at the first end, a second round section arranged at the second end, and a flat section that extends between the first round section and the second round section.

In some examples, the spring is defined by the flat section.

In certain examples, the flat section includes a serpentine segment that defines the spring.

In some cases, the spring is configured to provide a maximum restoring force of 40 to 60 grams.

In certain cases, the relaxation mask includes an electronics enclosure and a light diffuser disposed within a first one of the cavities. A coupling member couples the light diffuser to the electronics enclosure. The coupling member defines a channel and the spring is disposed within the channel.

In some implementations, the relaxation mask includes: at least one biometric sensor that is configured to output data associated with a subject wearing the relaxation mask; an electroacoustic transducer supported by the earpiece; a memory coupled to a processor; and instructions stored in the memory. The instructions, when executed, cause the processor to: output, via the electroacoustic transducer, an acoustic stimulus; receive the output data from the at least one biometric sensor; correlate the output data and the acoustic stimulus to identify a racing mind state; adjust the acoustic stimulus of the relaxation mask in response to the identified racing mind state; and output the adjusted acoustic stimulus via the electroacoustic transducer.

Another aspect provides a relaxation mask that includes a main body that defines a pair of eye cavities. At least one biometric sensor is configured to detect a biometric signal from a subject wearing the relaxation mask. An in-ear earpiece configured to output audio signals. Wiring couples the in-ear earpiece to the main body. A spring is configured to bias the earpiece towards the main body. The relaxation mask also includes a memory coupled to a processor. Instructions are stored in the memory. When executed, the instructions cause the processor to: output, via in-ear earpieces, an acoustic stimulus; receive output data from the at least one biometric sensor; correlate the output data and the acoustic stimulus to identify a racing mind state; execute an artificial intelligence (AI) program that adjusts the acoustic stimulus provided in response to the identified racing mind state; and output the adjusted acoustic stimulus via the in-ear earpieces.

Implementations may include one of the above and/or below features, or any combination thereof, further comprising:

In some implementations, the relaxation mask also includes a light diffuser that is disposed within a first one of the cavities. A coupling member couples the light diffuser to the electronics enclosure. The coupling member defines a channel and the spring is disposed within the channel.

In certain implementations, the AI program adjusts a visual stimulus provided by the light diffuser of the relaxation mask in response to the identified racing mind state and the instructions further cause the processor to output the adjusted visual stimulus via the light diffuser.

In some examples, the wiring defines the spring.

In certain examples, the wiring includes a serpentine segment that defines the spring.

In some cases, the relaxation mask also includes a sleeve having a first open end and a second open end. The wiring passes through the sleeve and the sleeve is arranged to overlie a subject's temple region when the relaxation mask is worn. A high friction material is disposed on an inner surface of the sleeve and is arranged to inhibit movement of the wiring when the relaxation mask is worn.

Advantages of a smart relaxation mask that creates a closed-loop experience to help subjects relax, fall, and stay asleep will be apparent from the description and the claims.

BRIEF DESCRIPTION OF THE DRAWINGS

FIG. 6A is a rear view of the relaxation mask of FIG. 1.

DETAILED DESCRIPTION

Figure 1:
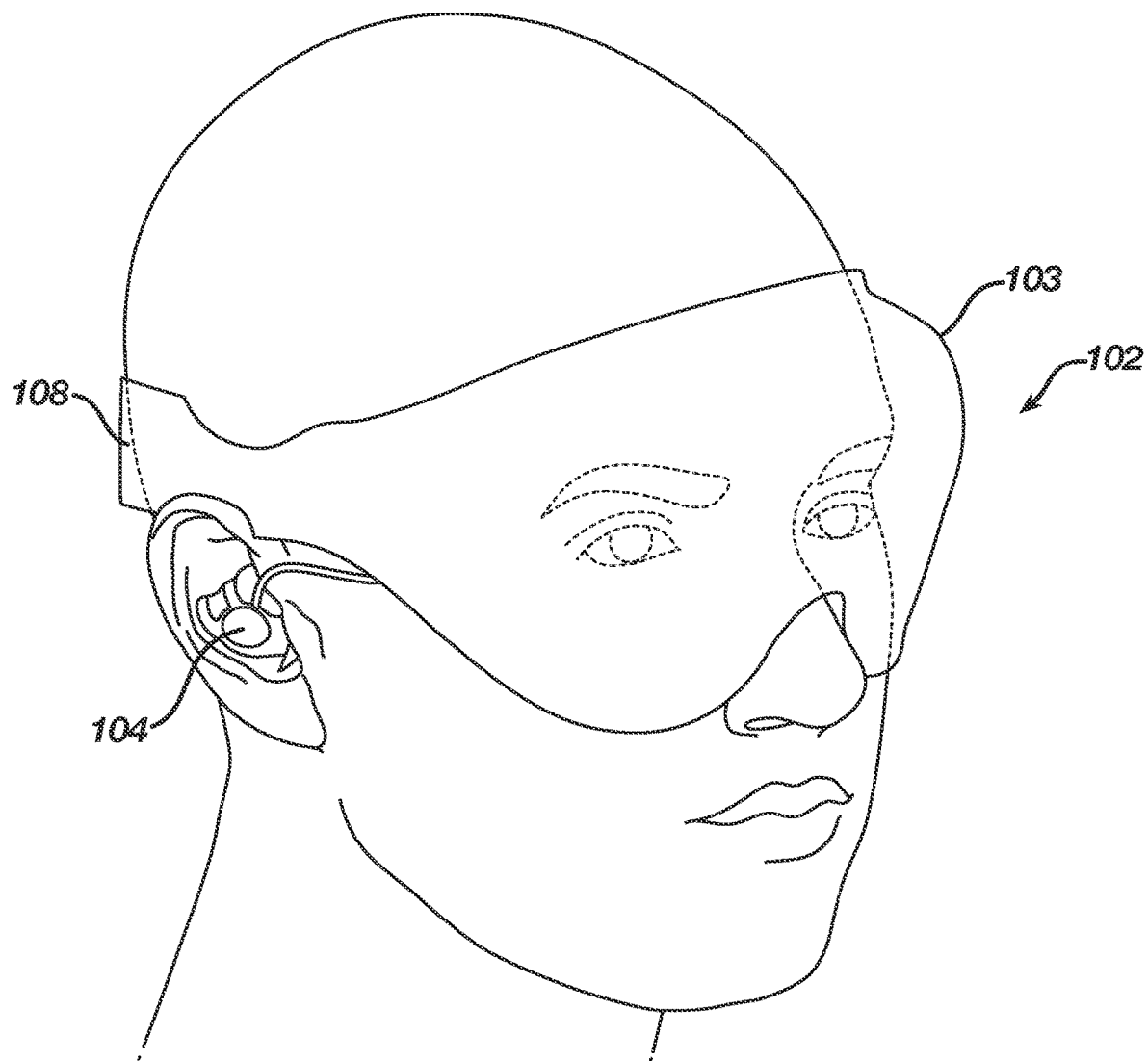
FIG. 1 illustrates an example of a smart relaxation mask on a subject.

A racing mind is characterized by racing thoughts. Racing thoughts may also be referred to as cognitive noise. Racing thoughts may focus on a single topic or several lines of thought. A subject with a racing mind ruminates over anxious thoughts, worries about something that has happened in the past, or worries about something that may happen in the future. In an example, a subject has racing thoughts about a phobia, an upcoming, potentially stressful situation, or an embarrassing moment. A racing mind may be overwhelming, increase anxiety and feelings of unease, and disrupt concentration. A subject struggles to relax, and fall and stay asleep because they have a racing mind and are ruminating on racing thoughts.

People use distraction techniques in an attempt to draw attention away from racing thoughts. Distraction techniques may help a subject focus on something that is external. Focusing on external, and perhaps more boring, thoughts help people fall asleep.

Relaxation strategies, playing music or a podcast, meditating, reading aloud, exercising, and humming are examples of distraction techniques that attempt to shift a subject's attention away from intrusive racing thoughts. Individual meditation requires some effort to focus. Guided meditation attempts to help a subject focus and guide the subject through a meditation exercise guided by a coach, written text, sound recording, video, or audiovisual media including music and/or verbal instruction.

The benefits of distraction techniques, including guided meditation, are achieved if a subject is focusing on the distraction. In an example, the distraction replaces the subject's racing thoughts, allowing the subject to relax, and eventually fall asleep. Because people are not always successful in focusing on the distraction, they may be affected by racing thoughts despite deliberate efforts and techniques to avoid them.

Aspects of the present disclosure provide a smart relaxation mask that enables closed-loop, multi-sensorial cognitive noise masking. The mask includes one or more biosensors and in-ear headphones, although around-ear, on-ear, and open-air (a/k/a "open-ear") headphone configurations are also contemplated. As explained in more detail below, the mask is configured to output a multimodal sensory stimulus. The sensory stimulus may be auditory, haptic, visual, or any combination thereof. The mask monitors one or more of the subject's biometric parameters. By comparing the sensory stimulus to the subject's biometric parameters, the mask identifies if the subject is in a racing mind state. If so, the mask adjusts an output of the mask in an effort to displace racing thoughts and guide the subject to sleep.

Adjusting the output based on an identified racing mind state exposes the subject to stimulus when needed to help guide the subject to a relaxation state. Accordingly, a subject is not exposed to unnecessary stimulus from the mask, which may have negative effects on the subject.

In aspects, with the help of an artificial intelligence (AI) virtual sleep coach and a learning algorithm executed by software in communication with the mask, the mask tracks the output of mask and associated changes in biometric parameters. The mask correlates the type and content of the sensory stimulus output with identified, biophysical markers in the subject's monitored biometric parameters. In an example, the biophysical markers indicate a drop in the subject's attention. In aspects, the mask tracks which sensory output or combination of sensory outputs were successful in capturing the subject's attention. In aspects, the mask uses this historical information to output a similar content in an effort to displace racing thoughts in the future mind wandering episode and guide the subject to a state of relaxation.

FIG. 1 illustrates an example of a smart relaxation mask 102 on a subject. In FIG. 1, a front view of the mask 102 is shown on a subject. The mask 102 covers the subject's eyes and decreases or blocks the perception of light emitted from external disturbances in the subject's environment.

The mask 102 blocks or attenuates sound from the subject's environment. The mask includes integrated, in-ear headphones 104, 106. In FIG. 1, a right in-ear earpiece 104 is shown. The mask includes a similar in-ear earpiece 106 for the subject's left ear (illustrated in FIG. 2). In an example, the in-ear earpieces include a substantially frusto-conical sealing structure configured to create a gentle seal with the subject's ear canal. The headphones are configured to block or attenuate sound from the subject's environment. The headphones are also configured to output an audio stream. The audio output may include, for example, music, a voice narrative, or a soundscape. In an aspect, the in-ear headphones are configured to perform one or more of active noise reduction and active noise cancellation. The smart mask is used to assist a subject's meditation. During a break between classes, meetings, or in an effort to reduce anxiety, the active noise reduction circuitry helps block noise and facilitate a meditation exercise.

As illustrated in FIG. 1, in aspects, the mask 102 wraps around the subject's head. In aspects, a strap 108 fits around the subject's head. The mask 102 has a low profile around the subject's temples.

Figure 2:
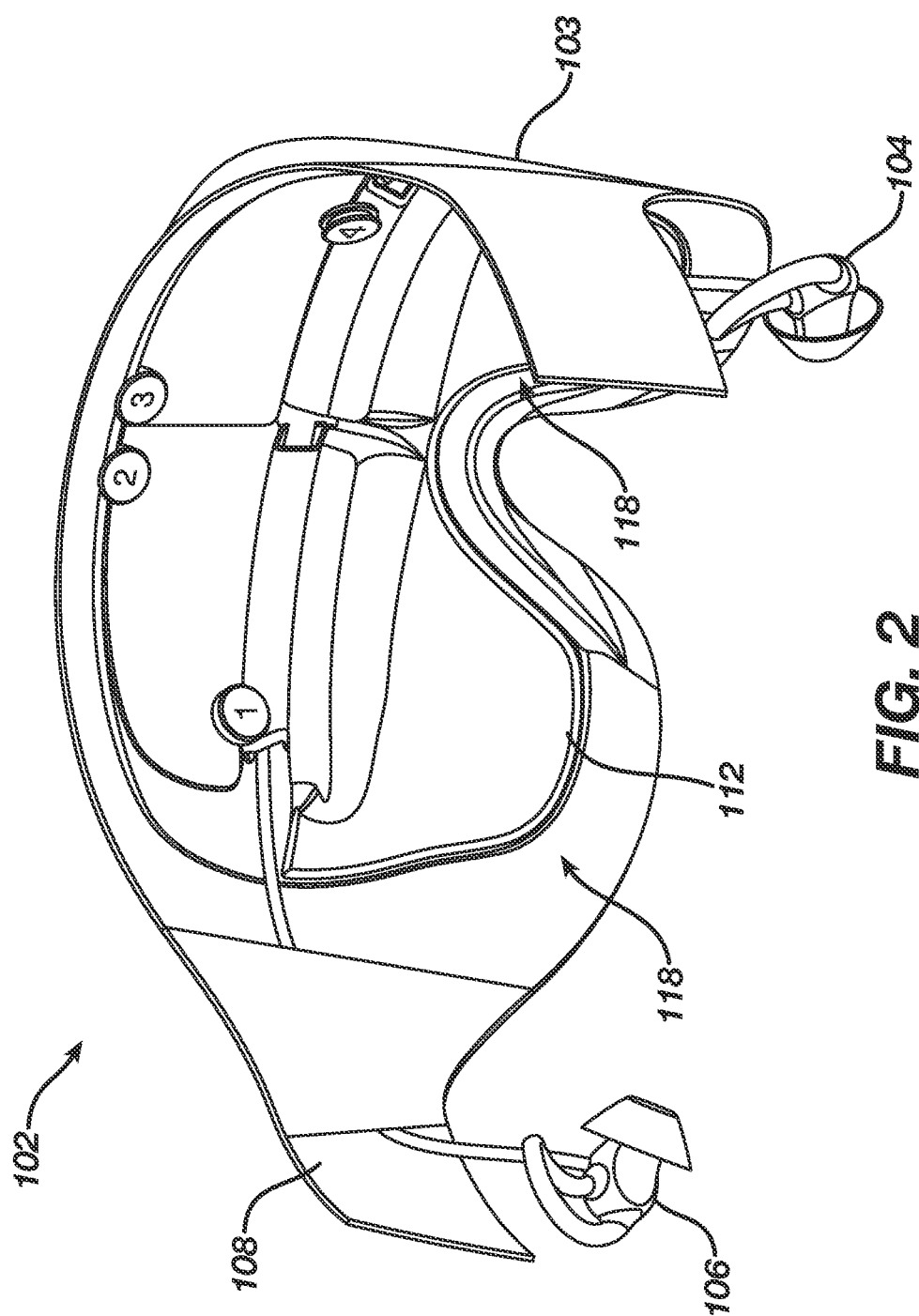
FIG. 2 illustrates an example of the backside of the smart relaxation mask, when the mask is not positioned on a subject.

FIG. 2 illustrates an example of the backside of the smart relaxation mask 102, when the mask is not positioned on a subject. As described with respect to FIG. 1, the mask 102 includes left 106 and right 104 in-ear earpieces. The mask includes a strap or band 108 that extends around a subject's head (as shown in FIG. 1).

In aspects, the mask includes biometric electrodes or sensors. Sensors and electrodes may be used interchangeably herein. Non-limiting examples of biometric sensors include an electroencephalogram (EEG) sensor, electrooculogram (EOG) sensor, electrocardiogram (ECG) sensor, galvanic skin response (GSR) sensor, photoplethysmography (PPG) sensor, electromyogram (EMG) sensor, inertial motion (IMU) sensor, heart rate sensor, heart rate variability (HRV) sensor, respiration rate (RR) sensor, accelerometer, gyroscope, microphone, or other suitable sensor. Output from sensors are used to identify a subject's neurological markers that indicate or estimate when a subject's attention is drifting. Attention drifting may indicate the subject is in a state of rumination and is not focusing on the sensory stimulus output by the mask. The mask alters an output to displace drifting thoughts and refocus the subject's attention to the output of the mask.

As shown in FIG. 2, electrodes may be placed on one or more of contact points 1-4, the earpieces 104, 106, or any other location on the mask. The contact points 1-4 are located above the forehead. In aspects, at least a portion of the contact points 1-4 collect signals from one or more of the frontal cortex or the prefrontal cortex. One or more electrodes, such as a subset of electrodes located on or near contact points 1-4 collect an EEG signal from the frontal cortex or prefrontal cortex and the other electrodes on or near contact points 1-4 collect signals from the forehead of a subject wearing the mask 102.

Figure 3:
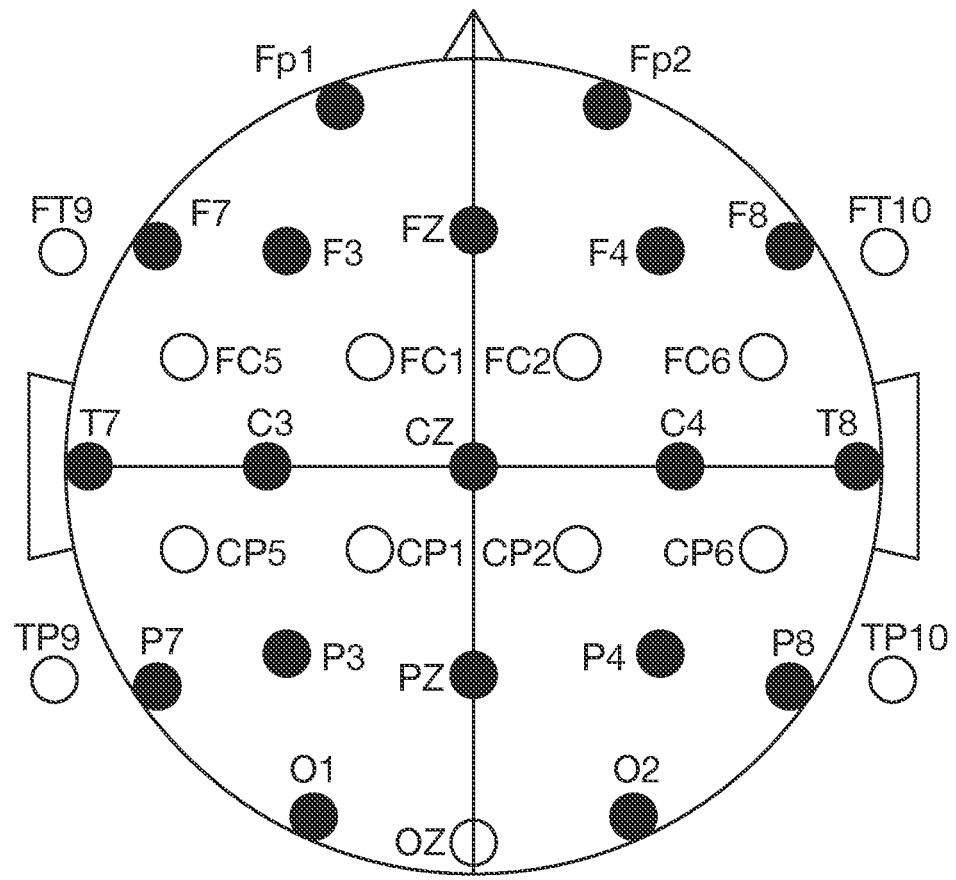
FIG. 3 illustrates an example of electrodes in the context of an EEG test according to the Modified Combinatorial Nomenclature (MCN) system.

FIG. 3 illustrates an example of sensor placement in the context of an EEG test according to the Modified Combinatorial Nomenclature (MCN) system. The MCN system is an internationally recognized system to describe the location of scalp electrodes to ensure standardized reproducibility. The electrode locations consist of letters and numbers. The letters (F, T, P, O) generally indicate the underlying lobe (frontal, temporal, parietal, and occipital) and "C" indicates the central region. Odd numbers refer to electrode placement on the left side of a head; even numbers refer to electrode placement on the right side of the head; and electrodes in the midline are annotated with "z" for zero. In addition to these, the letter codes, Fp indicates the prefrontal (or frontal pole) sites and TP indicates an area between the temporal and parietal lobes.

The form factor of the mask 102 allows placement of sensors in locations that are rich in biometric information. The collected biometric information is used to identify when a subject's attention is drifting. Drifting attention indicates the subject's focus is moving away or has moved away from the output of the mask. The subject's attention may have shifted towards anxious thoughts, making it difficult for the subject to relax, fall, and/or stay asleep.

In one example, the form factor of the mask allows electrodes to be placed near the frontal cortex or prefrontal cortex, which is rich in biometric information. The frontal lobe is covered by the frontal cortex. The frontal part of the frontal cortex is covered by the prefrontal cortex. The frontal cortex performs diverse functions loosely called cognition. The prefrontal cortex manages learning, mental states, and concentration. In an example, electrodes are disposed on the mask and contact Fp1 and Fp2 (FIG. 3). In an example, any of the contact points 1-4 (FIG. 2) may contact Fp1 and Fp2. The form factor further allows electrodes to be placed near the auditory cortex. Signals collected from the auditory cortex exhibit increased electrical activity in response to a subject listening or focusing on auditory stimulus. In an example, the left 106 and right 104 in-ear earpieces include conductive ear tips that make good contact with TP9 and TP10. Accordingly, in aspects, one or more biometric sensors are disposed on the ear tips of the in-ear earpieces 104, 106.

Figure 4A:
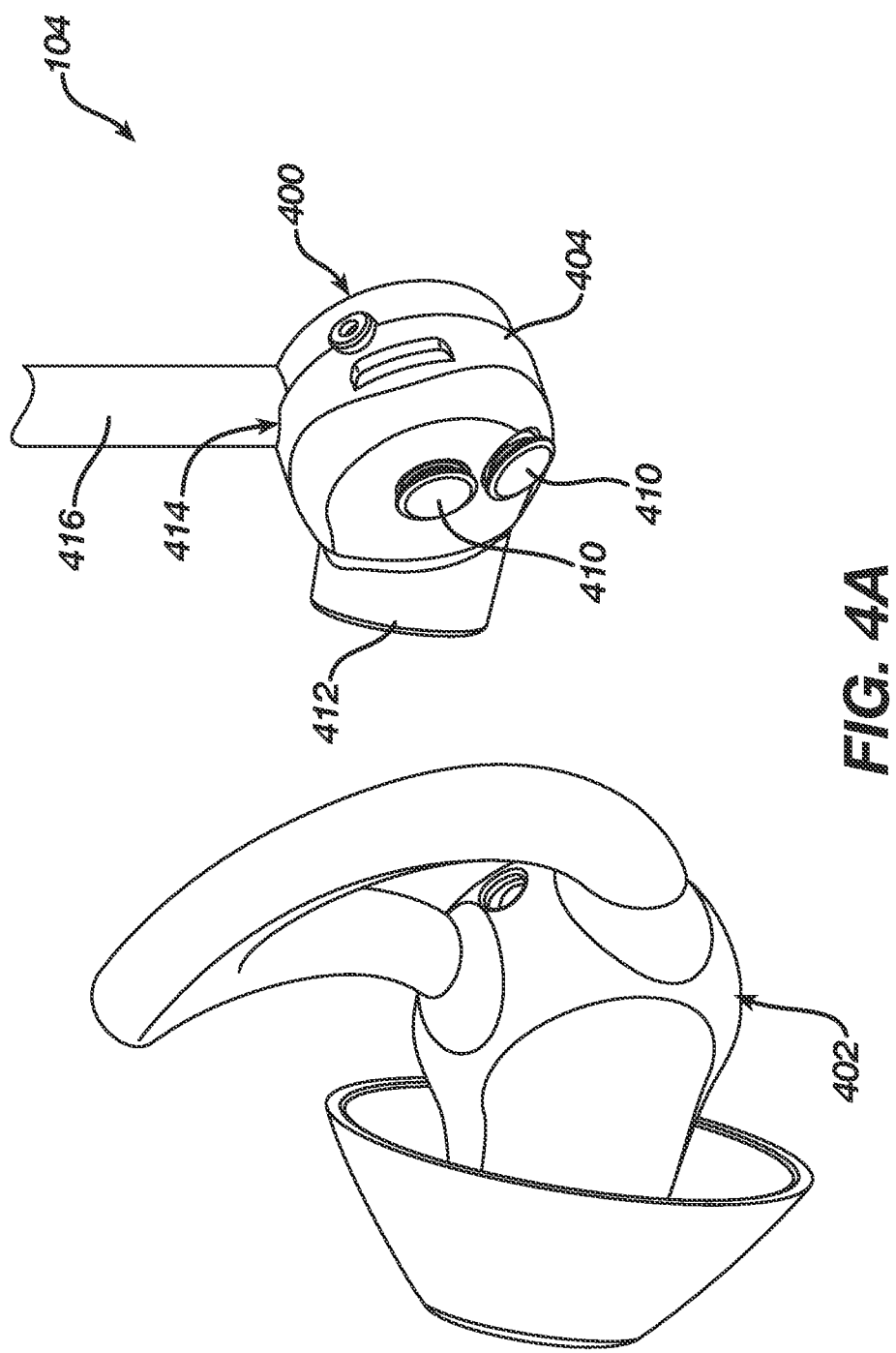
FIG. 4A is an exploded perspective view of an earpiece of the smart relaxation mask of FIG. 1.
Figure 4B:
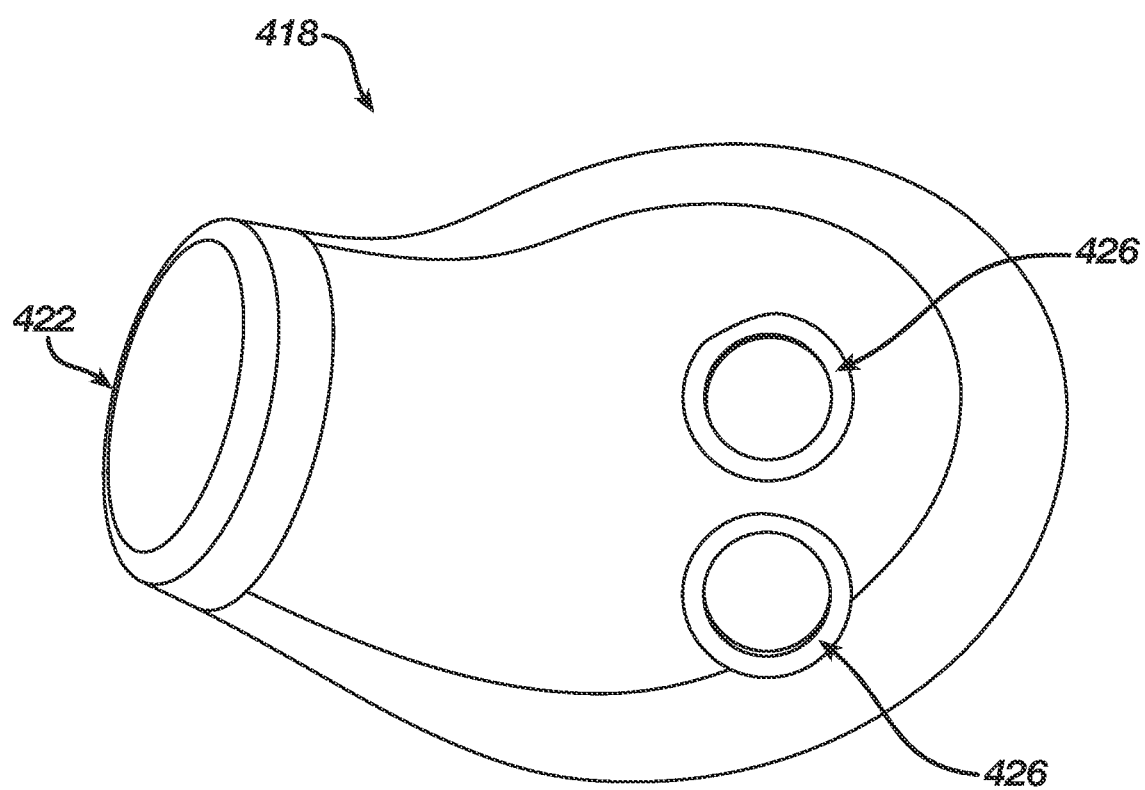
FIGS. 4B & C are front and rear views, respectively, of a first portion of an eartip from the earpiece of FIG. 4A.
Figure 4C:
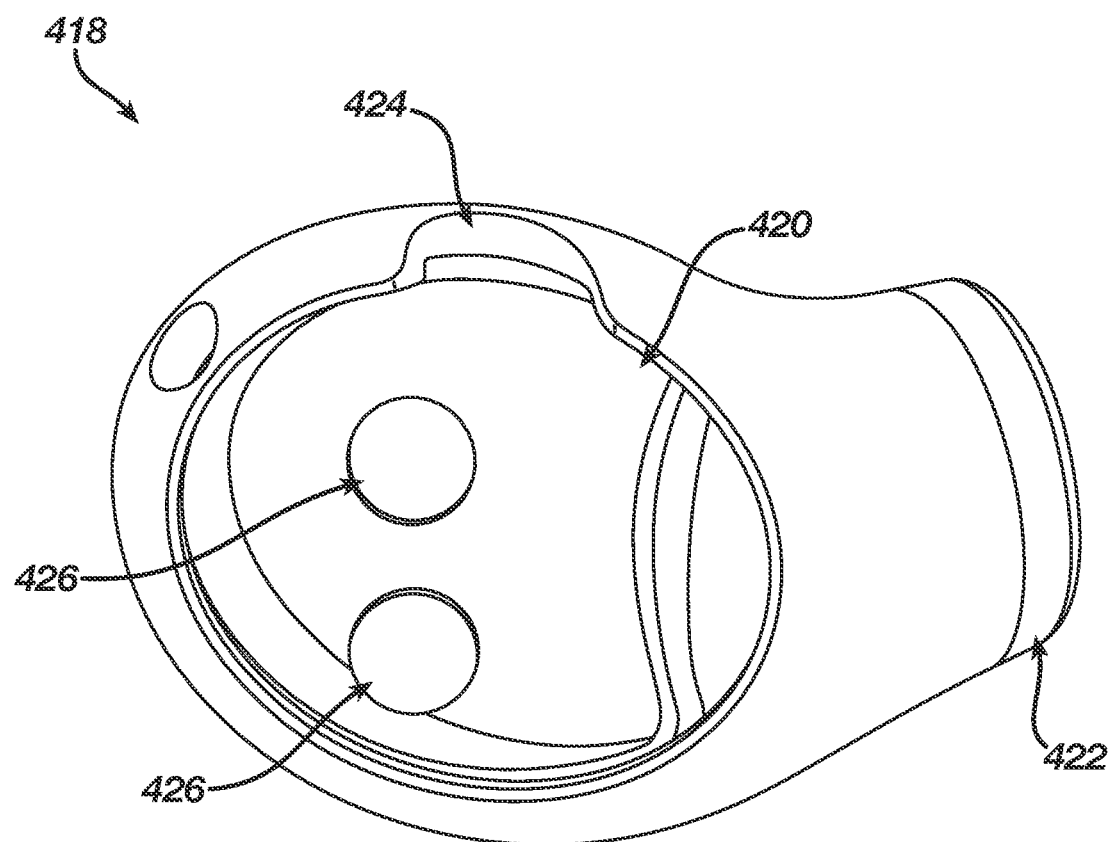
FIG. 4D is a rear view of the earpiece of FIG. 4A.
FIG. 4E is a cross-sectional view of the earpiece of FIG. 4D, taken along line 4E-4E.
Figure 4D:
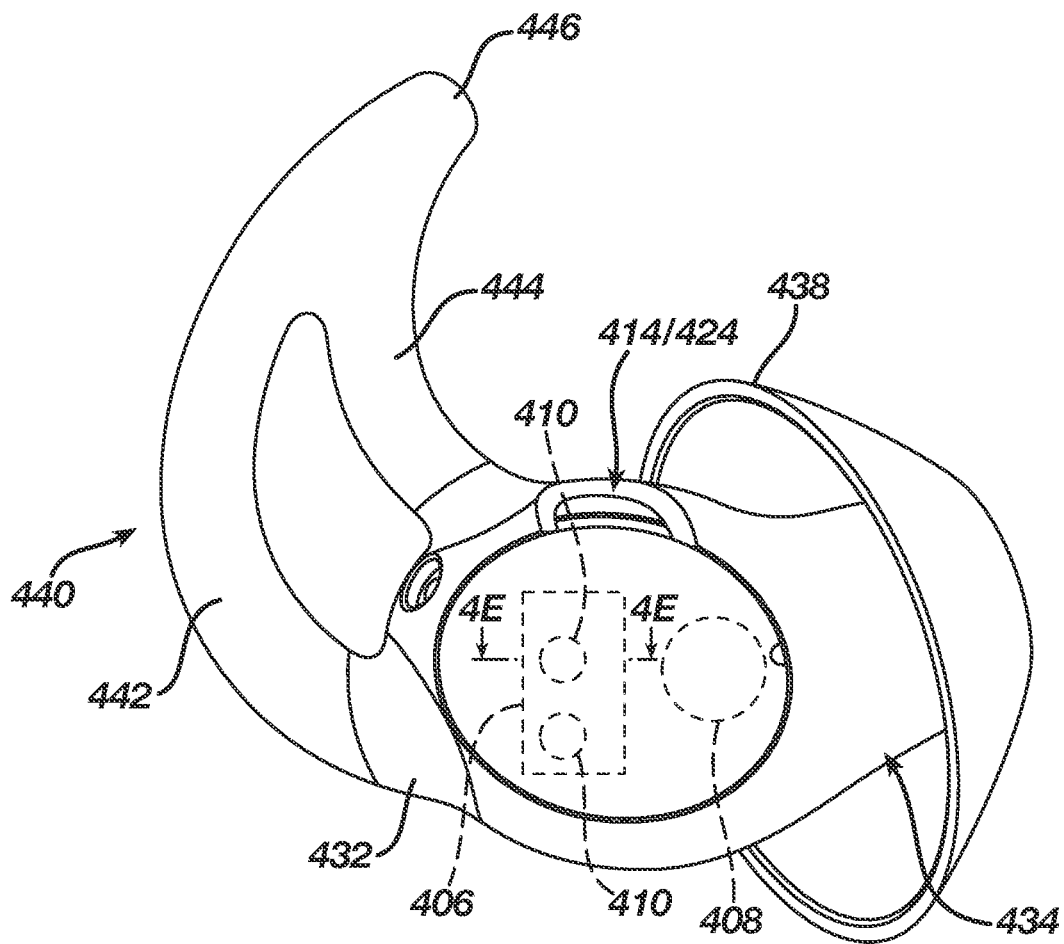

The in-ear earpieces 104, 106 may both have a similar construction. In that regard, FIGS. 4A through 4E illustrate an exemplary construction of one of the in-ear earpieces, but the construction described with respect to those figures is equally applicable to the other earpiece. With reference to FIG. 4A, each earpiece 104, 106 (right earpiece 104 shown) includes an earbud 400 and an eartip 402. The earbud 400 includes a rigid housing 404 that carries a printed wiring board (PWB 406, FIG. 4D) and a transducer 408 (FIG. 4D). The PWB 406 supports a pair of electrically conductive pogo pins 410, e.g., gold pogo pins, which extend through and outwardly from the housing 404. The housing 404 defines a first nozzle portion 412 that is configured to allow acoustic energy radiated from the transducer 408 to pass therethrough. The housing 404 also defines a wiring receptacle 414 that is configured to receive wiring 416 for powering the transducer 408 and for reading electrical signals from the pogo pins 410, e.g., via the PWB 406. The housing 404 may have a two-piece construction and may be formed from a molded plastic such as acrylonitrile butadiene styrene (ABS), polycarbonate (PC), PC/ABS, polyamide (PA) 6,6, or PA 12.

The eartip 402 has an elastomeric cover that couples to the earbud 400 and provides a relatively soft contact surface for engaging the subject's ear. The eartip 402 is formed in a two-shot molding process. Referring to FIGS. 4B & 4C, a first portion 418 is formed in a first molding operation. The first portion 418 is formed with a firmer material that defines a cavity 420 (FIG. 4C) for receiving the earbud 400. The first portion 418 has a first durometer of about 50 Shore A to about 80 Shore A. Suitable material for forming the first portion 418 includes an unfilled liquid silicone rubber or high consistency rubber (silicone) containing a platinum catalyst. An example of this material is Shin-Etsu KE 1950-70, available from Shin-Etsu Silicones of America, Akron, Ohio. The first portion 418 need not be formed of silicone. Other elastomeric materials such as a thermoplastic elastomer, thermoplastic urethane, a thermoset urethane, a fluroelastomer such as FKM are also suitable for forming the first portion 418.

The first portion 418 also defines a second nozzle portion 422 that is configured to couple to the first nozzle portion 412 in the earbud 400. A recess 424 (FIG. 4C) is arranged to accommodate the wiring 416 coupled to the earbud 400. A pair of apertures 426 are formed in the first portion 418. The apertures 426 are arranged to overlie the pogo pins 410 when the earbud 400 is received in the cavity 420. First ends 428 (FIG. 4E) of a pair of electrically conductive plugs 430 are inserted into respective ones of the apertures 426 before a second portion 432 (FIG. 4D) of the eartip 402 is formed. The electrically conductive plugs 430 (FIG. 4E) help to provide a low impedance electrical path between the pogo pins 410 and the second portion 432 of the eartip 402. The electrically conductive plugs 430 may be formed, e.g., machined, of an electrically conductive metal, such as gold.

The second portion 432 (FIG. 4D) is formed around the first portion 418 in a second molding operation. The second portion 432 is formed of a softer material, i.e., softer than the material used to form the first portion 418, that is doped with a conductive material (e.g., carbon nanoparticles such as multi-walled carbon nanotube (MWCNT), silver coated carbon nanoparticles, silver coated glass particles, graphene oxide, graphene, edge oxidized graphene oxide). The second portion 432 has a second durometer of about 20 Shore A to about 60 Shore A. The second portion 432 may include between 2.5% and 6%, e.g., 5%, conductive material by weight. A suitable material for forming the second portion 432 is available under the tradename ELASTOCYL™ HTV1001, available from Nanocyl SA of Sambreville, Belgium.

In one example, between 25% and 60% by weight of the conductive masterbatch (Elastocyl HTV1001), which itself contains 10% (MWCNT) by weight, was combined with an unfilled, uncatalyzed high consistency rubber (silicone) commonly abbreviated as an HCR. The unfilled silicone was HCR silicone known as 10 Shore A available from Able-One Systems Inc. of Kitchener, Ontario, Canada. The total amount of MWCNT was calculated based on the 10% by weight in the masterbatch and the % by weight of masterbatch added to the total mix. This calculates to 2.5%-6% MWCNT/weight.

This material was blended through use of heat to make the material more workable, and compression with a heated hydraulic press to force the two materials together, and through rolling with a 2 roll mill to encourage mixing. After the material was combined and before it was molded, a Peroxide catalyst was added to the material for it to cure. The peroxide overcomes the carbon's tendency to inhibit a platinum or tin cured silicone. The catalyst used was Luperox® 231, 1,1-Bis(tert-butylperoxy)-3,3,5-trimethylcyclohexane but could also be peroxide catalysts such as Luperox® 101, 2,5-Bis(tert-butylperoxy)-2,5-dimethylhexane, or similar, as well as Dicumyl Peroxide. Luperox® 231 and Luperox® 101 are available from Arkema Inc., King of Prussia, Pa.

Still other polymeric composites (e.g., rubbers compounded with conductive fillers such as carbon black, carbon nanotubes, graphene, silver, glass-coated silver), and/or intrinsically conductive polymers (e.g., poly(3,4-ethylenedioxythiophene) polystyrene sulfonate or PEDOT:PSS), may be used to form the second portion 432. The second portion 432 need not be formed of a fully conductive material, but, instead, may be formed of a material, e.g., an elastomer, with a conductive coating such as described in co-pending U.S. patent application Ser. No. 16/448,849, filed May 30, 2019. The complete disclosure of which is incorporated herein by reference.

The second portion 432 defines a third nozzle portion 434 that surrounds and extends the first and second nozzle portions 412, 422 formed in the earbud 400 and first portion 418 of the eartip 402, respectively. The first, second, and third nozzle portions 412, 422, 434 together define a nozzle that provides an acoustic path for acoustically coupling the transducer 408 to a subject's ear canal. The second portion 432 also defines an umbrella-shaped tip 438 that surrounds the nozzle and is configured to engage a subject's ear canal. In the illustrated example, the second portion 432 also defines a positioning and retaining structure 440 that includes an outer leg 442 and an inner leg 444. The outer leg 442 is curved to generally follow the curve of the anti-helix at the rear of the concha of the subject's ear. Distal ends of the legs 442, 444 are joined at a point 446.

Figure 4E:
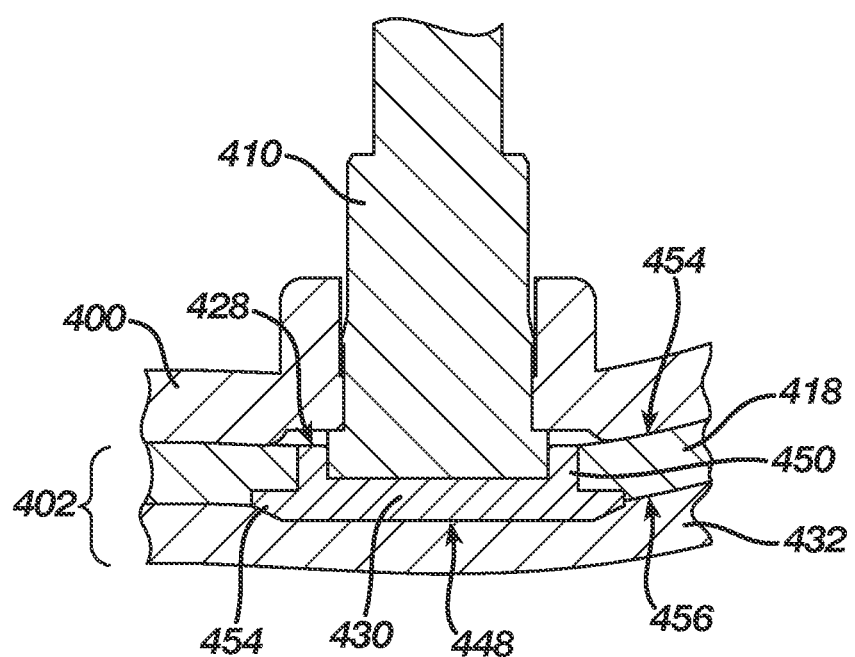

As shown in FIG. 4E, the second portion 432 of the eartip 402 is molded over the first portion 418 such that it covers and encapsulates second ends 448 (one shown) of the electrically conductive plugs 430 forming a tight bond therebetween. The electrically conductive plugs 430 may each include a shaft 450 that extends from the first end 428 to a head 454 at the second end 448. The head 454 may be configured to overhang the shaft 450. The electrically conductive plugs 430 may be configured such that the first ends 428 sit substantially flush with a first surface 454 of the first portion 418 of the eartip 402 and such that a bottom surface of the head 454 rests against the first portion 418. In this implementation, the second portion 432 is molded around the first portion 418 and the electrically conductive plug 430 such that the second portion 432 contacts the top surface and peripheral side edge(s) of the head 454 of the plug 430. The second portion 432 is thus bonded to the electrically conductive plugs for electrical contact. The eartip 402 serves as an electrode that couples to the subject's ear for EEG measurements. The second portion 432 completely covers the electrically conductive plugs 430 along the outer surface of the eartip 402 so that no hard surfaces are in direct contact with the subject's skin.

Figure 5:
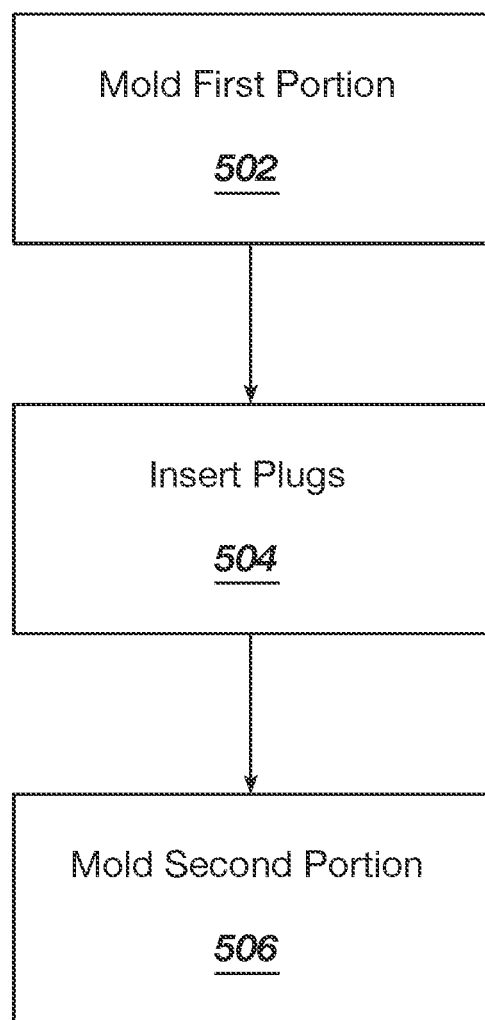
FIG. 5 is an exemplary process for forming an eartip.

FIG. 5 illustrates an exemplary process 500 for forming the eartips 402. At 502, a first elastomer, e.g., silicone, is molded using a first mold in a first molding operation to form the first portion 418 of the eartip 402. The first forming operation may include compression molding, transfer molding, or liquid injection molding. At 504, one or more electrically conductive plugs are inserted into apertures 426 that are formed in the first portion 418 in the first molding operation. At 506, the first portion 418, carrying the inserted plugs 430, is placed into a second mold and a second, electrically conductive elastomer, e.g., a silicone doped with electrically conductive carbon nanoparticles, is molded using the second mold in a second molding operation to form the second portion 432 of the eartip 402 directly on top of the first portion 418 and electrically conductive plugs 430. The second molding operation may include compression molding, transfer molding, or liquid injection molding.

With reference to FIG. 6A, the mask 102 includes a main body 103 that defines a pair of eye cavities 118. The main body 103 may be formed of a fabric, such as a 2-way stretch knit fabric. The eye cavities 118 serve as light barriers that cover the subject's eyes. In an example, a light diffuser 112 outputs light that the subject receives through closed eyelids. The light diffuser 112 may be disposed, at least partially around or near the eye cavities 118.

In an aspect, the light diffuser 112 creates a gentle light-based, wake-up experience. In one example, the light diffuser is associated with an alarm application executed on the mask or a paired device. At a pre-determined time before the alarm is set to go off, the light diffuser begins to imperceptibly glow and the intensity of the light slowly increase, mimicking a beautiful sunrise. In an example, the light diffuser 112 outputs lights to create a light-based relaxation or entrainment experience. The light-based relaxation experience or entrainment experience may be either open-loop or closed-loop based on a subject's biometric parameters. For an open-loop experience, a subject may instruct the relaxation mask, by a voice activated command or user input, to begin a light-based relaxation exercise. For a closed-loop experience, the light output is adjusted, at times in combination with other sensory stimulus, to relax the subject and entrain breathing.

Figure 6B:
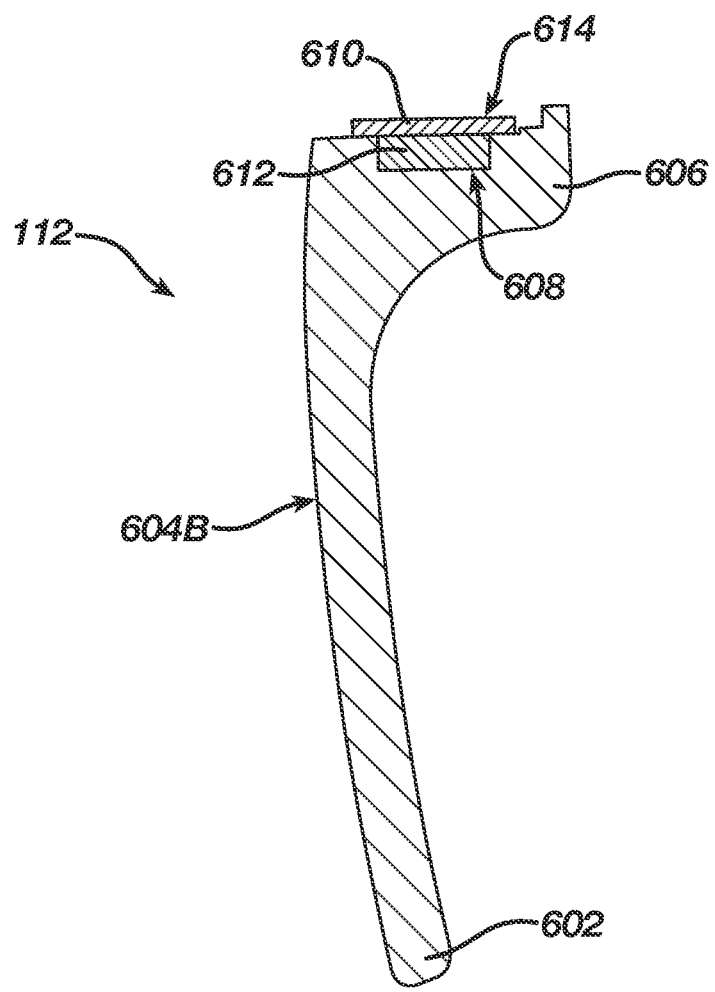
FIG. 6B is a cross-sectional side view of a light diffuser.

The light diffuser 112 is configured to output light that the subject receives through closed eyes. With reference to FIGS. 6A & 6B, the light diffuser 112 includes a main body portion 600 that defines a pair of lenses 602 (i.e., left and right lenses) that are disposed in the eye cavities 118 with one lens 602 in each cavity 118. The lenses 602 generally have the shape of an eye-patch or eyeglass lens (e.g., an "aviator" lens shape). Each of the lenses 602 has a first (front) surface 604 (FIG. 6B) with a convex curvature that coincides with a concave curvature of the corresponding eye cavity 118. The lenses 602 are dimensioned to cover an interpupillary distance (IPD) for a range that includes a $5^{th}$ percentile female IPD to a $95^{th}$ percentile male IPD across ethnicities including Anglo, Asian, African, and Hispanic so as to inhibit (e.g., prevent) interference with the subject's eyes including eye lids and eye lashes.

The light diffuser 112 also defines a pair of ledges 606 arranged along respective top edges of the lenses 602 and extending substantially perpendicular thereto. A small recess 608 (FIG. 6B) is provided in each of the ledges 606 for receiving a printed circuit board 610 carrying an LED 612, collectively referenced as "PCB/LED assembly 614," for illuminating the corresponding one of the lenses 602. The recesses 608 help to properly locate the PCB/LED assemblies 614 during assemblage. The PCB/LED assemblies 614 are held in place within the corresponding recesses 608 via a pressure sensitive adhesive. Each LED 612 is arranged to fire downward into the top edge of a corresponding one of the lenses 602. A gap 618 is provided between the two ledges 606 to allow the light diffuser 112 to flex to conform the shape of the subject's head.

Figure 6C:
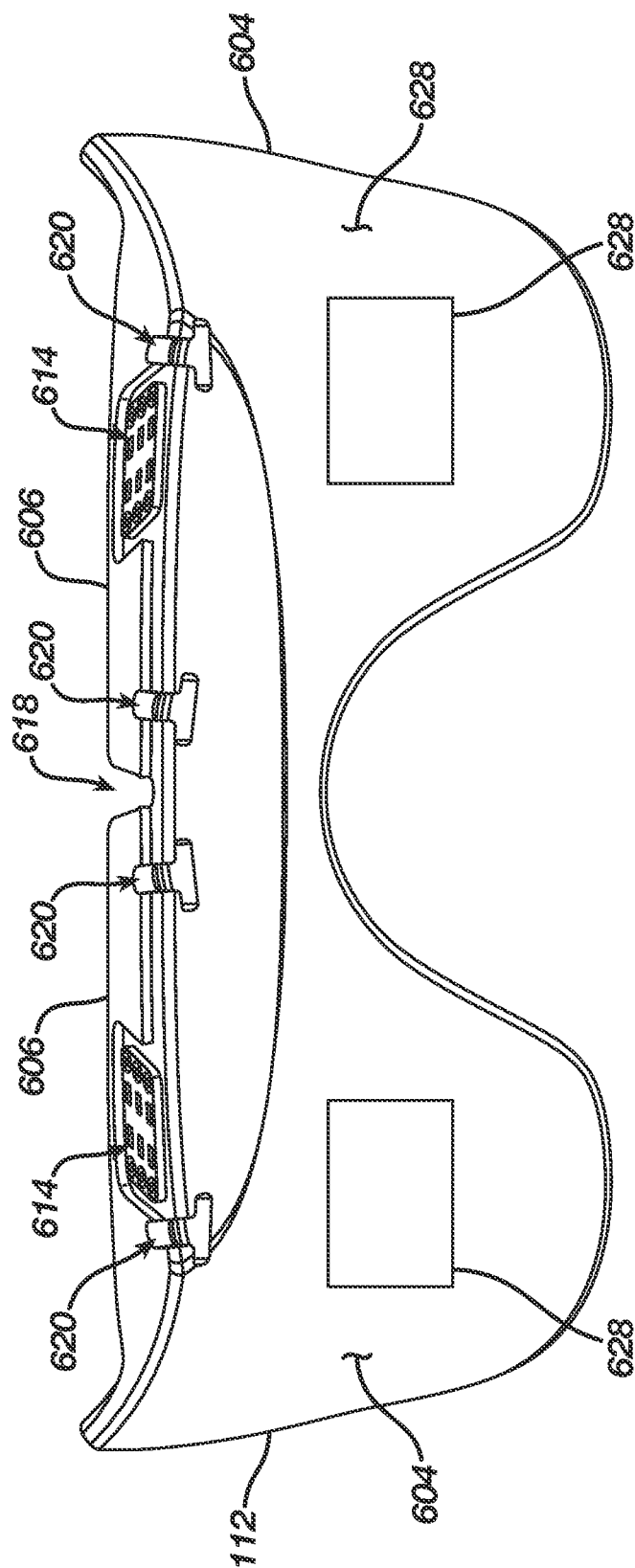
FIG. 6C is a front view of the light diffuser of FIG. 6B.
Figure 6D:
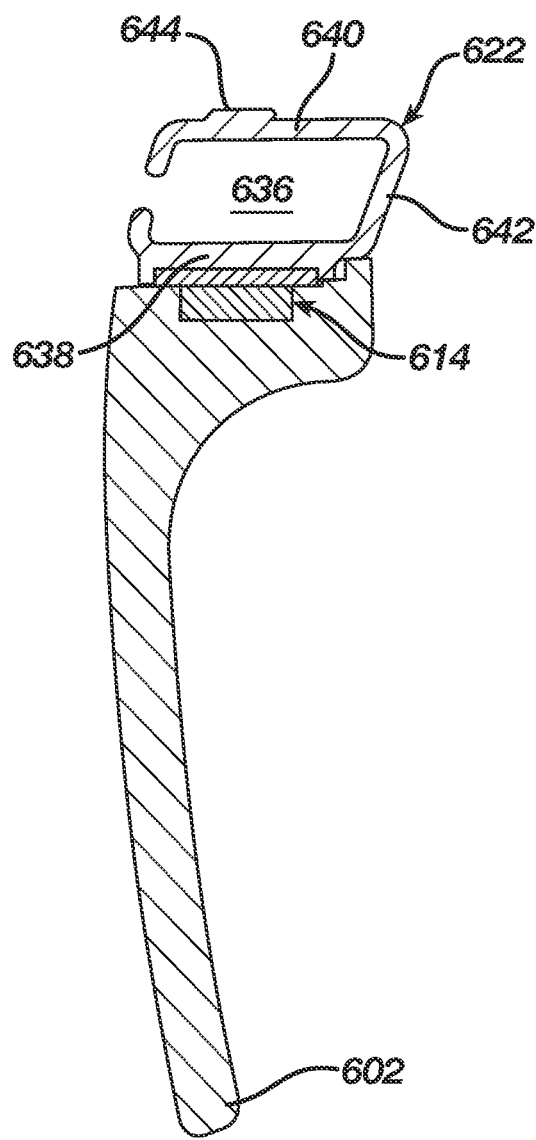
FIG. 6D is a cross-sectional side view of a light diffuser and coupling member.

With reference to FIGS. 6C and 6D, the light diffuser 112 defines a plurality of attachment points 620 for coupling the light diffuser 112 to a pair of coupling members 622 (a/k/a "diffuser posts"). The plurality of attachment points 620 may include slots (e.g., t-slots) that are configured to receive mating features 626 (e.g., t-shaped protrusions, FIG. 6E) on the coupling members 622. In some cases, a hook-and-loop type fastener 628, e.g., as sold under the tradename Velcro, may be provided on the first surface 604 of the light diffuser 112 (e.g., along the respective convex curves of the lenses 602) to help couple the light diffuser 112 to the corresponding eye cavity 118 along the inner surface of the mask 102. The light diffuser 112 is formed of silicone and may include a diffusive additive to control opacity. A suitable silicone for forming the light diffuser 112 is DragonSkin™ 30 from Smooth-On, Inc of Macungie, Pa. This is a 30 durometer platinum cure silicone. The material grade and durometer could be any silicone that has any amount of translucency to it when cured and can be any durometer that silicone is capable of being. Another example of a similar material but in liquid silicone rubber form is Shinetsu 1950-30A, available from Shin-Etsu Silicones of America, Inc. of Akron Ohio.

In some cases, the light diffuser 112 may be molded from silicone including between 0% and 30%, e.g., 1% to 30%, e.g., 15% to 30%, diffusive additive by volume. A suitable diffusive additive is White Pigment: Silc Pig silicone pigment from Smooth On. Other white pigment that is capable of being dispersed in silicone may work. For example, suitable Light Diffusing Powders include: MSS-500, MSS-500H, MSS-500 W, MSS-500/3, MSS-500/3H, MSS-500/3N, MSS-500/20N, and MSS-500N-FS, available from Kobo Products Inc. of South Plainfield, N.J.; Revlon PhotoReady Powder in Translucentobo Products, and Revlon PhotoReady Perfecting Primer available from Revlon, Inc. of New York, N.Y.; and Dermablend Loose Setting Powder in Translucent, available from L'Oréal S.A. of Paris, France. Still other powders or liquids that possess light diffusing properties and area capable of being loaded into the silicone may be used.

While the illustrated implementation shows male attachment points (i.e., mating features 626) on the coupling member and female attachment points (i.e., slots 620) on the light diffuser, in other implementations, the diffuser may include one or more male attachment points and the coupling member may include one or more female attachment points for receiving the one or more male attachment points on the light diffuser.

Figure 6E:
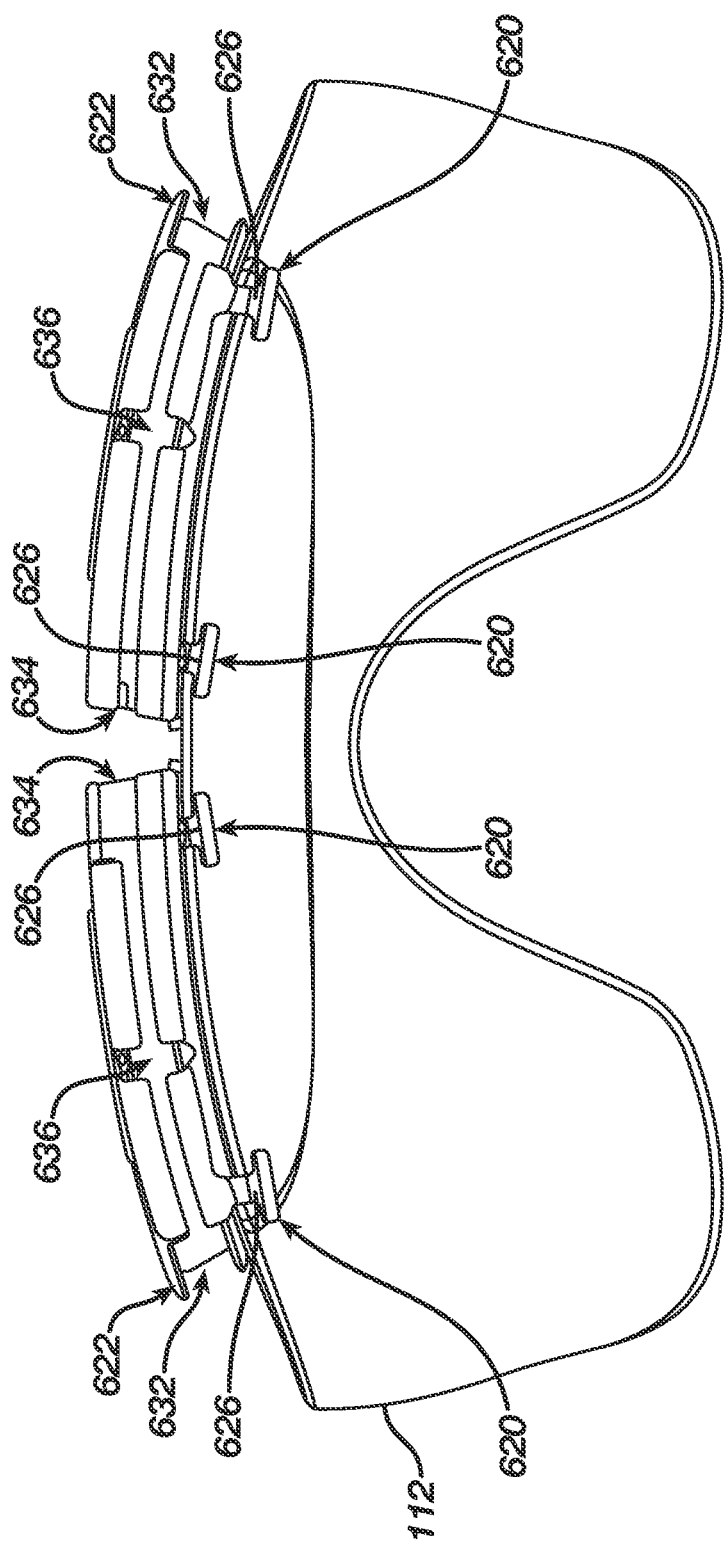
FIG. 6E is a front view of a light diffuser and coupling members.

The light diffuser 112 is coupled to an electronics enclosure 630 (FIG. 6A) via the coupling members 622. Referring to FIGS. 6D and 6E, each of the coupling members 622 includes a first open end 632. a second open end 634, and a channel 636 extending therebetween. Each of the coupling members 622 includes a bottom wall 638, a top wall 640, and one or more sidewalls 642 extending therebetween. In the illustrated example, the attachment features 626 extend downward from the bottom wall 638 and may be formed integrally therewith. Each of the coupling member 622 may also include a protrusion 644 that extends outwardly from the top wall 640. The protrusions 644 are configured to rest within respective mating recesses formed in the electronics enclosure 630 to assist with alignment during manufacture. The top walls 640 of the coupling members 622 are bonded to the electronics enclosure 630, e.g., with a pressure sensitive adhesive. The coupling members 622 are formed, e.g., molded, from a rigid material, e.g., a rigid polymer, such as HP 3D High Reusability PA 12, available from HP Inc., Palo Alto, Calif. The HP PA12 is a 3D printable material that may be 3D printed using HP's Multi-jet Fusion process. In an injection molded form of this part, any polyamide 12 (PA12 or Nylon 12) could be used as well as any PA 6,6. Other materials that could be used are Acrylonitrile Butadiene Styrene (ABS), Polycarbonate (PC), PC/ABS, Ultem 1000 series poly etherimide (PEI).

In some cases, wiring from the electronics enclosure 630 to the PCB/LED assembly 614, i.e., for powering and controlling the LED 612, is run through one of the open ends 632, 634. Alternatively, or additionally, one or more openings may be provided in one or more sidewalls 642 of the coupling member 622 to accommodate wiring for the PCB/LED assembly 614. The channel 636 also helps to accommodate the wiring 416 (FIG. 4A) for a corresponding one of the in-ear earpieces 104, 106.

In aspects, the mask includes one or more mechanisms to output a haptic stimulus. In one example, the mask includes a tactile motor configured to vibrate. The motor may be located along the strap 108, above the subject's temporal region, or anywhere else on the mask 102.

It may be desirable to provide a mask 102 that will accommodate different head geometries and sizes, e.g., from the $5^{th}$ percentile female head to the $95^{th}$ percentile male head. For the headphones 104, 106, one critical dimension is the distance from the *glabella* (i.e., the skin between the eyebrows and above the nose) to the tragus. In order to accommodate different size heads, slack can be provided in the wiring 416. However, excess slack can disturb the subject, e.g., by dangling and irritating the subject's face. Excess slack can also result in tugging, e.g., as the subject moves during the night, and can even cause the attached earbud 400 to be pulled out of the subject's ear if it gets caught up on something.

To help address this issue, the wiring 416 is designed such that it automatically retracts to prevent slack from forming outside of the mask 102. In that regard, a serpentine segment 700 (FIG. 7A) is formed in the wire itself. The serpentine segment 700 acts as a tension spring and retracts the wire slack into the mask 102. When the earpiece 104, 106 is received in the ear canal, the tension force on the tragus (40-60 grams max), attributable to the serpentine segment 700, helps with mask stability—it can also help to keep the earpiece 104, 106 firmly engaged with the subject's ear canal.

Figure 7A:
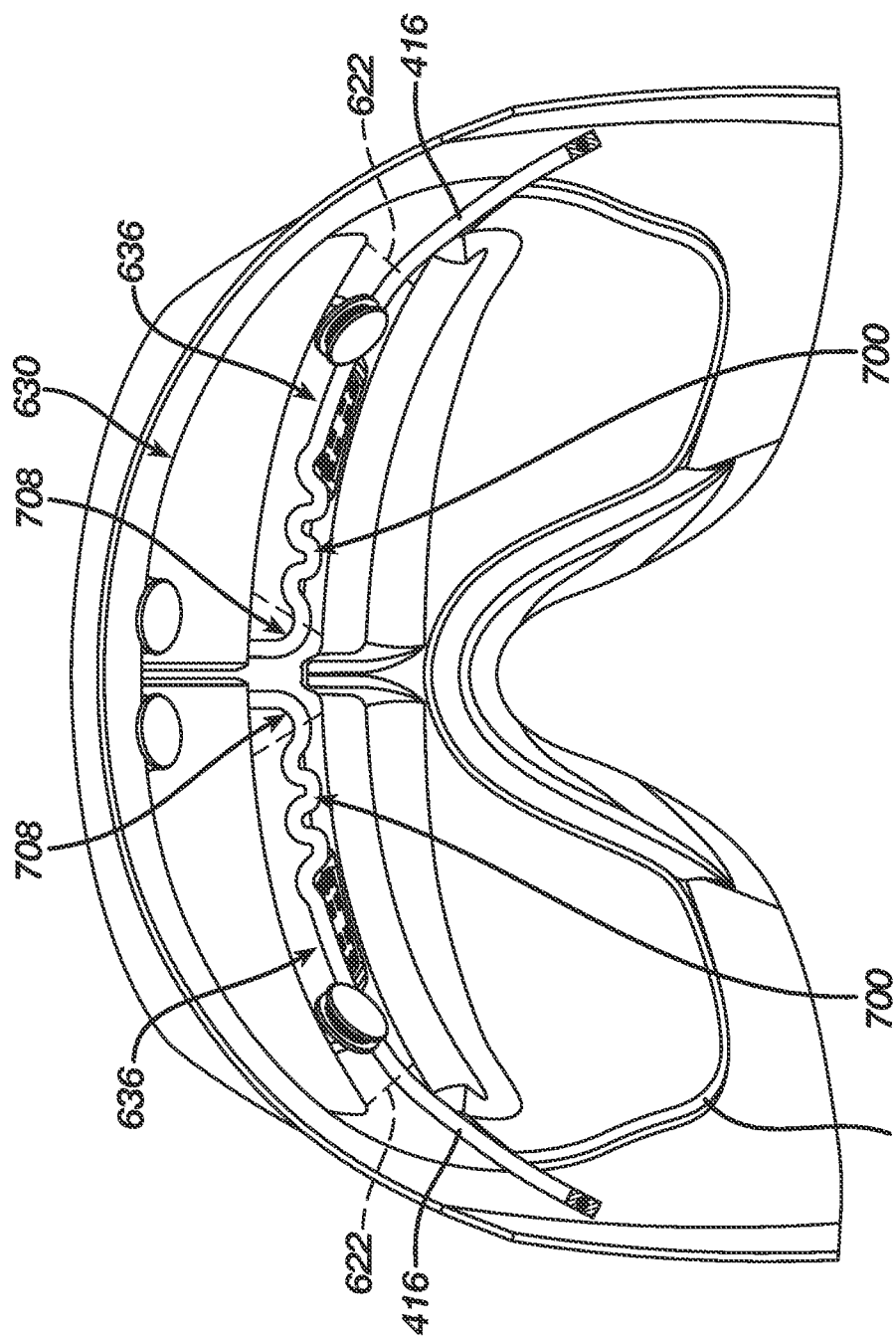
FIG. 7A is a rear view of the relaxation mask of FIG. 1 showing wiring for the earpieces.
Figure 7B:
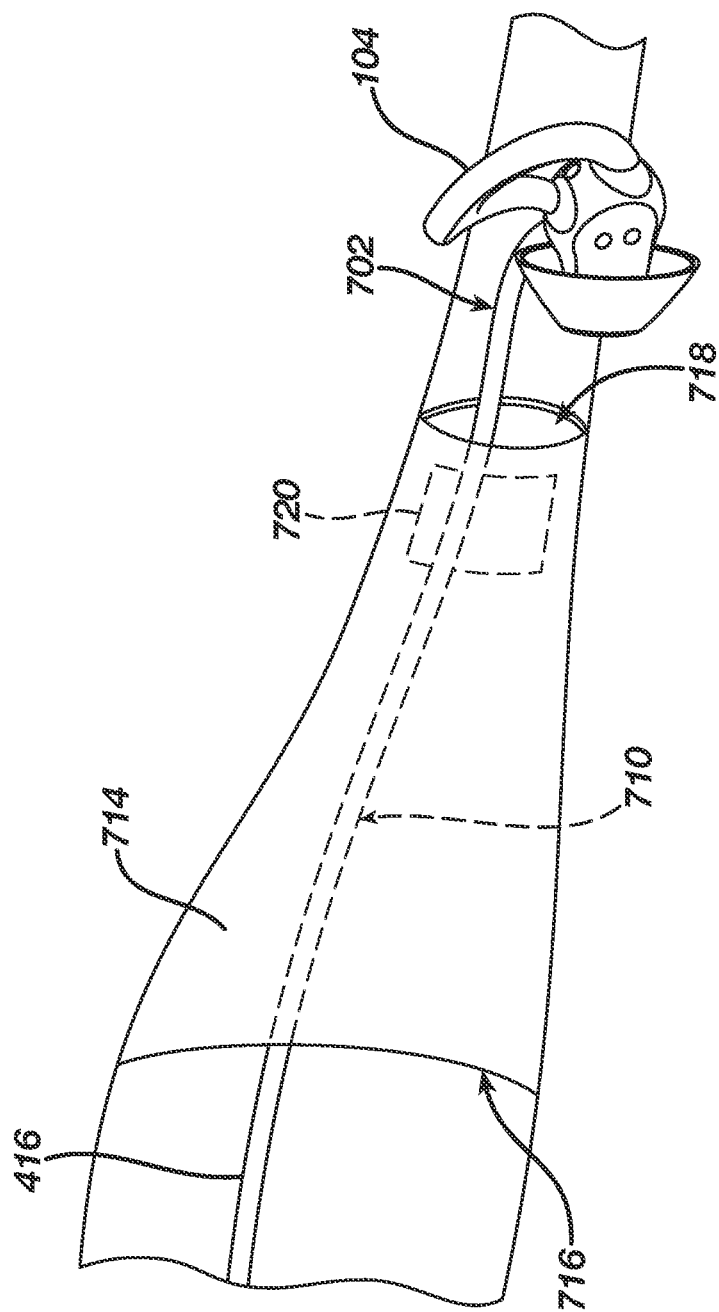
FIG. 7B is a detailed rear view of a temple region of the relaxation mask of FIG. 1.
Figure 7C:
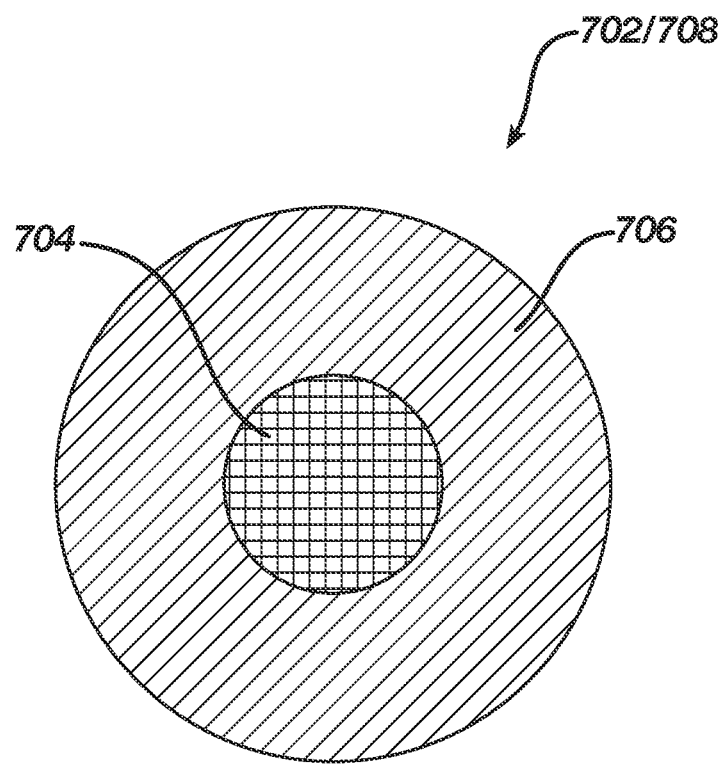
FIG. 7C is a cross-sectional view of a round section of the wiring for the earpieces.

The serpentine segment 700 may be about an inch in length and, is accommodated in the channel 636 formed in a corresponding one of the coupling members 622 (shown in hidden lines in FIG. 7A). The serpentine segment 700 may be formed by molding an elastomer (e.g., silicone, thermoplastic elastomer (TPE), or thermoplastic urethane (TPU)) around the conductive wire (e.g., 35-38-gauge filament wire) in the serpentine shape. In some cases, the wiring 416 may have both round and flat elastomer sections. A first round section 702 (FIG. 7B) is provided at the interface with the corresponding earpiece 104, 106 to allow that region to be able to bend and rotate to accommodate various ear geometries. In some cases, the wiring 416 is arranged such that it sits in a notch between a tragus and a helix of the subject's ear. With reference to FIG. 7C, the first round section 702 includes a portion of the conductive wire 704 surrounded by a portion of elastomer 706 having a circular cross-section having a diameter, d, of about 2 mm to about 2.2 mm.

Figure 7D:
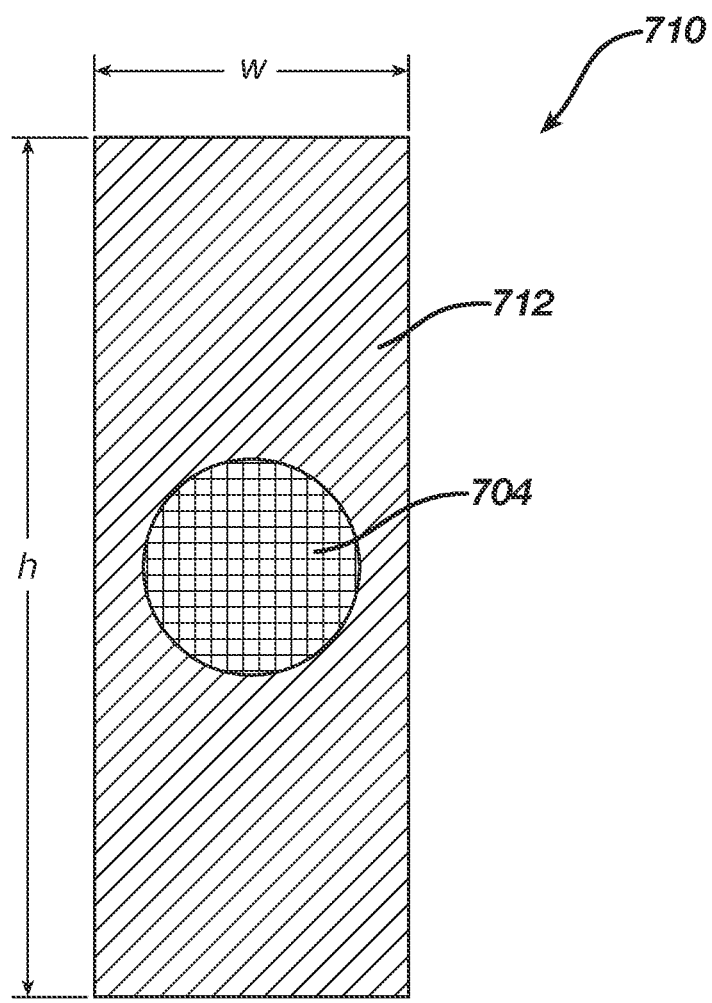
FIG. 7D is a cross-sectional view of a flat section of the wiring for the earpieces.

A second round section 708 (FIG. 7A) is provided within the mask, at the interface where the wiring 416 enters the electronics enclosure 630. It may be easier to form a sweatproof seal with a round wire at that location. In between the round sections 702, 708 is a flat section 710 (FIG. 7B); i.e., a substantially round filament wire surrounded by a substantially flat elastomer. The flat elastomer may have a rectangular cross-section. This allows the section of wire that lies along the side of the subject's head to lay flat so that the subject is less likely to feel it. The flat section 710 can also be beneficial for forming the serpentine segment 700. A flat wire serpentine segment may require lower force to extend and can accommodate a greater number of turns. With reference to FIG. 7D, the flat section 710 of the wiring 416 includes a portion of the conductive wire 704 surrounded by a portion of elastomer 712 having a substantially rectangular cross-section. In the implementation illustrated in FIG. 7D, the elastomer has a height, h, that is at least 2× the dimension of its width, w. While a flat section with a rectangular cross-section is shown and described, the flat section 710 may have other cross-sectional shapes. In one alternative example, the flat section 710 may have an elliptical cross-section, e.g., one in which the major axis of the ellipse is at least 2× the dimension of its minor axis.

In some implementations, the mask 102 includes a sleeve 714 (FIG. 7B) that is formed near the temple region (i.e., the region designed to overlie a subject's temple) of the mask 102. The sleeve 714 may be formed by a piece of fabric that is stitched to the main body 103 of the mask 102 leaving two open ends through which the wiring 416 for the corresponding one of the earpieces 104, 106 is threaded. The sleeve 714 helps to cushion the subject's head from the wiring 416. A first open end 716 is arranged towards the forehead region of the mask 102, near the electronics enclosure 630. A second open end 718 is arranged near the attachment point for the head strap 108. In some implementations, a high friction material 720 (e.g., an elastomer) is provided on one or more of the inner surfaces of the sleeve 714. In one example, the high friction material is located near the second open end 718. The high friction material 720, together with pressure applied by the subject's head when the mask 102 is worn, helps keep the wiring 416 in place. The sleeve 714 and high friction material 720 may be utilized as an alternative or in addition to the serpentine segment 700 to assist in managing slack in the wiring 416.

Figure 8:
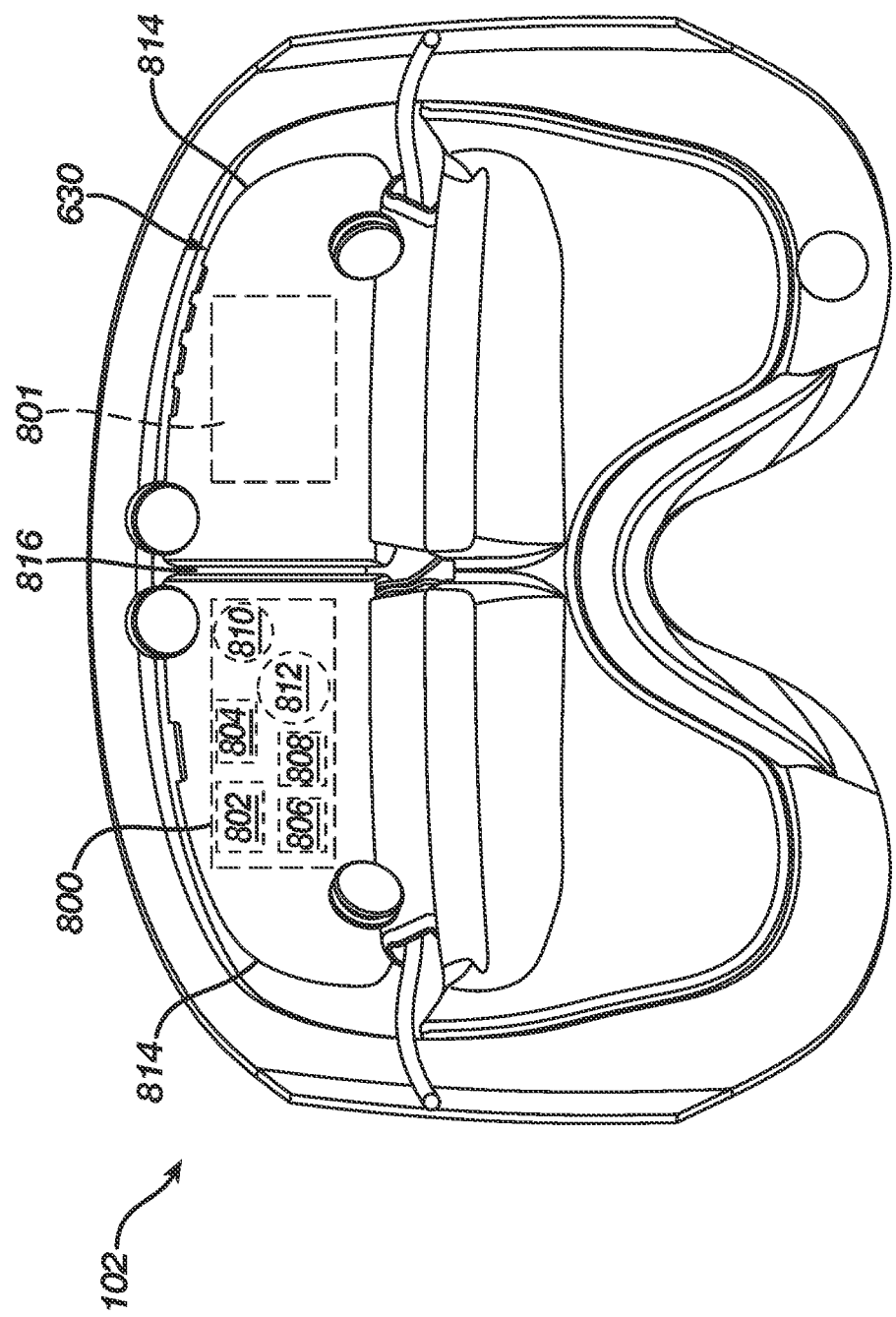
FIG. 8 is a rear view of the relaxation mask of FIG. 1 highlighting an electronics enclosure.

With reference to FIG. 8, the electronics enclosure 630 contains electronics 800 and a battery 801. The electronics 800 may include any combination of a memory 802 and processor 804, communication unit 806, a transceiver 808, a microphone 810 and a tactile motor 812. The electronics enclosure 630 includes a pair of enclosure segments 814, each enclosing a respective portion of the electronics and/or battery, which are electrically connected via a flexible electrical connection 816. The flexible electrical connection 816 may comprise one or more electrical wires and/or flexible printed circuitry. Splitting the electronics enclosure 630 into multiple (e.g., two) discrete enclosure segments 814 allows the electronics enclosure 630 to better conform to the subject's facial geometry. The enclosure segments 814 may be formed of a hard plastic. For improved comfort, the electronics enclosure 630 may be disposed behind a flap of fabric and/or cushioning.

The processor controls the general operation of the mask 102. For example, the processor performs process and control for audio and/or data communication. The processor is configured to measure, receive, calculate, or detect at least one biometric parameter of the subject. In aspects, the processor executes an AI program that takes action to regain a subject's attention by adjusting an output of the mask. In aspects, the AI program performs functions of a personalized sleep coach.

In combination with the audio output transducers in the earpieces 104, 106, the processor is configured to output a sensory stimulus. The processor receives the output data from at least one biometric sensor. The processor, optionally in combination with a wireless communication unit, correlates the output data and the sensory stimulus to identify a racing mind state. In response to an identified racing mind, the processor, in combination with the transducers, haptic motor, and/or light diffuser 112 adjusts and outputs one or more of an adjusted auditory, haptic, or visual stimulus. The biometric sensors are configured to continuously monitor a subject's biometric parameters in an effort to determine if the subject remains in a racing mind state. If so, the processor, in combination with the transducer, haptic motor, and/or light diffuser 112 adjusts an output of the mask to regain the subject's attention and displace wandering thoughts. As described in more detail below, the mask has the ability to output multi-modal outputs. Upon determining that the subject remains in a racing mind state, the mask varies the type of sensory output or outputs a combination of sensory outputs.

The communication unit facilitates a wireless connection with one or more other wireless devices, such as with other devices in the subject's vicinity. For example, the communication unit may include one or more wireless protocol engines such as a Bluetooth engine. While Bluetooth is used as an example protocol, other communication protocols may also be used. Some examples include Bluetooth Low Energy (BLE), NFC, IEEE 802.11, WiFi, or other local area network (LAN) or personal area network (PAN) protocols. The mask 102 may wirelessly receive audio files or processed information associated with dips in attention via the communication unit. Additionally, or alternatively, the communication unit may receive information associated with a subject's biometric parameters, obtained via a contactless sensor, such as a radio frequency (RF) sensor, a radar sensor, or an under-the-bed accelerometer The transceiver transmits and receives information via one or more antennae to exchange information with one or more other wireless devices. The transceiver may be used to communicate with other devices in the subject's vicinity, such as a bedside unit, a smartphone, and/or a smartwatch. The transceiver may receive a sensory stimulus to be output by the relaxation mask from an external wireless device or a network.

The transducers convert electrical signals into sound. The transducers are configured to output an auditory stimulus to a subject. The auditory stimulus may be, for example, a guided meditation exercise, soundscape, or music. The transducers output audio signals, including adjusted audio signals in an effort to displace racing thoughts.

Figure 9:
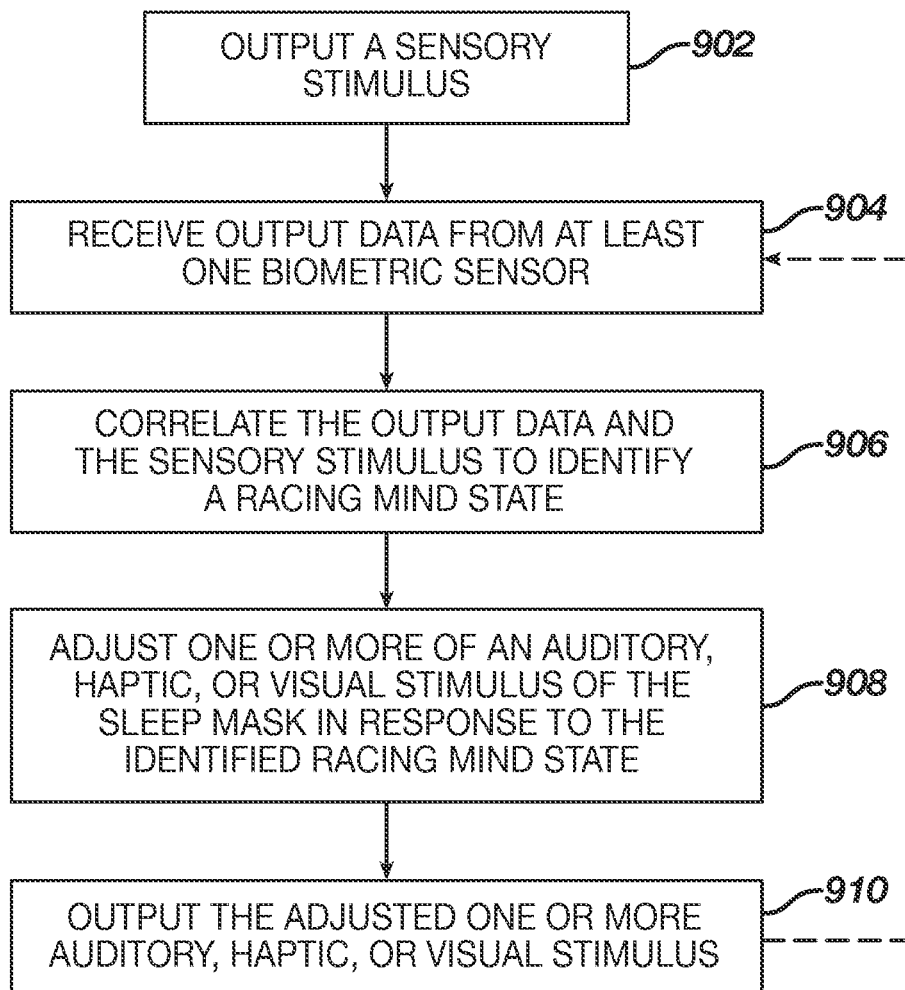
FIG. 9 illustrates example operations performed in accordance with aspects described herein.

FIG. 9 illustrates example operations 900 performed by a relaxation mask, such as the mask 102. At 902, the mask outputs, via an electroacoustic transducer, a sensory stimulus. In aspects, the sensory stimulus includes a guided meditation track, a soundscape, or music. In an example, the sensory stimulus has at least an auditory component output via in-ear earpieces.

At 904, the mask receives output data associated with a subject (a/k/a user) wearing the mask. The output data is obtained using at least one biometric sensor. The output data includes information collected using one or more biometric sensors. The biometric sensors include any combination of, for example, electrodes or sensors configured to collect or determine an EEG, EOG, ECG, GSR, or PPG. In an example, and EEG signals is collected from the frontal cortex or the prefrontal cortex. Other signals are collected from the forehead. In aspects, the EEG signal is collected from the frontal cortex or the prefrontal cortex and another signal is collected from the auditory cortex.

At 906, the mask correlates the output data and the sensory stimulus to identify if the subject has a racing mind. In aspects, a processor onboard the mask processes the output data, for example, to determine an Engagement Index and identify any dips in the Engagement Index. In aspects, the mask transmits an indication of the data to an external device or a network. Examples of external devices include a cell phone, computer, tablet, or any smart device. The external device or network processes the output data and transmits the processed data to the mask. The mask correlates the processed data with the sensory stimulus to determine if the subject is paying attention to the sensory stimulus or if the subject's attention is drifting away from the sensory stimulus. If the subject's attention is drifting away from the sensory stimulus, the mask determines the subject is in a racing mind state. In aspects, output from multiple sensors and multiple types of sensors are used in combination to determine, with increased confidence, if a subject has a racing mind.

Additional details on how an EEG signal may be used to determine a racing mind state is described in U.S. patent application Ser. No. 16/363,695, filed Mar. 25, 2019, which published as U.S. patent application publication no. 2020/0306493 on Oct. 1, 2020. The complete disclosure of which is incorporated herein by reference.

If the subject is determined to have a racing mind, at 908, the mask adjusts one or more of an auditory, haptic, or visual stimulus. At 910, the mask outputs the adjusted one or more auditory, haptic, or visual stimulus.

In one example, the sensory stimulus output at 902 includes an auditory output. At 908, if the subject is determined to have a racing mind, the mask adjusts the stimulus by outputting lights via the light diffuser 112. In an aspect, the lights are modulated to correlate or coincide with the audio output. In an example, LED lights are flashed to match prompts by an AI program to help regain the subject's attention.

In another example, at 902, an AI program is describing an environment or setting that may be calming to the subject, such as a campfire setting. In an example, the AI program outputs sounds typically heard in a campfire setting, such as rustling leaves and burning wood. At 908, if the subject is determined to have a racing mind, the mask adjusts the stimulus by outputting lights via the light diffuser 112 that emulate the glow of a campfire. In an aspect, the subject is determined to have a racing mind. At 908, the mask adjusts the stimulus by introducing a haptic output such as a vibration in an effort to guide the subject to focus on the output of the AI program. In an aspect, if the subject is determined to have a racing mind, the mask changes the simulated environment, for example, from the campfire setting described above, to the sounds of waves rolling on a beach.

In aspects, as illustrated in FIG. 9, the mask continues to receive output data from at least one biometric sensor after outputting adjusted one or more auditory, haptic, or visual stimulus. The mask continuously correlates received output data from at least one biometric sensor and the adjusted one or more auditory, haptic, or visual stimulus to determine if the subject continues to have a racing mind. If so, the mask further adjusts and outputs at least one auditory, haptic, or visual stimulus. In aspects, when the subject is determined to be asleep, based on collected biometric information, the mask outputs masking sounds in an effort to block environment noises. In other aspects, the mask reduces sound pressure level of auditory stimulus and gradually stops outputting any visual or haptic stimuli. According to aspects, the mask eventually stops outputting a sensory stimulus and only outputs masking sounds.

The mask is configured to adjust any combination of auditory, haptic, or visual stimulus in an effort to recapture a subject's attention. The following description provides examples of output stimulus, determining the subject has a racing mind and adjusting the output stimulus based on an identified racing mind for illustrative purposes.

In an example, the sensory stimulus includes a low-frequency component that occupies, for example, frequencies in the range of approximately 20 Hz to 125 Hz. An EEG or other biometric parameters indicate if the subject is paying attention to the low-frequency component included in the sensory stimulus. Absence of activity in the EEG signal or other biometric signals indicate a subject's mind may be wandering. In response, to a wandering mind, the mask adjusts an output to regain the subject's attention.

In one example, the mask initially outputs an auditory stimulus such as a virtual sleep coach narrating a story. If one or more biometric parameters indicate the subject is in a racing mind state, the mask changes the type of auditory output. In an example, the virtual sleep coach stops narrating a story and begins a guided imagery exercise where the coach attempts to evoke mental images. In another example, the sleep coach continues the narrative, and the relaxation mask outputs lights modulated to correlate to the narrative. In yet another example, the sleep coach continues the narrative and a gentle haptic output is output by a tactile motor, in an effort to regain the subject's attention.

Despite the adjusted output, in aspects, the biometric parameters indicate the subject's attention is still wandering. In response, the relaxation mask further adjusts an output. In an example, the mask may adjust the speed of modulated lights, change the type of auditory output by starting a guided meditation, guided imagery exercise, or outputting music In aspects, the mask collects historical information regarding which output stimulus or combination of output stimuli regained the subject's attention and which output stimulus, or combination of output stimuli did not regain the subject's attention. Through a machine learning algorithm, this historical information is used to create a smart, adaptive system that intelligently selects how to adjust an output stimulus for a specific subject in response to a racing mind state.

In one example, the relaxation mask includes at least one EEG sensor configured to collect a signal from the subject's frontal or prefrontal cortex region. In an aspect, the relaxation mask outputs a sensory stimulus that is one of auditory, haptic, or visual. The relaxation mask receives output data from the EEG sensor. The relaxation mask correlates the output data with the sensory stimulus to identify when a subject has a racing mind. In response to an identified racing mind, an AI program adjusts an output of the relaxation mask and the relaxation mask outputs the adjusted output.

In an example, a relaxation mask includes a first electrode configured to detect an EEG signal from the frontal cortex of prefrontal cortex of a subject, a second electrode configured to detect at least one of an EOG signal, ECG signal, GSR, or PPG signal from the forehead region of the subject, in-ear earpieces configured to output audio signals, light diffuser(s) disposed within eye cavities of the relaxation mask, and a tactile motor disposed over the temporal lobe of the subject. The relaxation mask is configured to output an auditory sensory stimulus and correlate the EEG signal, the information obtained using the second electrode, and the sensory stimulus to determine if the subject is in a racing mind state. If so, the mask adjusts at least one stimulus based on the determined racing mind state and outputs the adjusted stimulus.

In an aspect, a microphone on the mask or on a paired device in communication with the mask detects noise in the subject's environment. One or more of: the mask, a paired device, or a network determines whether there is a correlation between noise detected by the microphone and measurements from information collected using one or more of the sensors. In an example, the microphone detects noise in the subject's vicinity correlates with an increase in the subject's EEG signal. In response, the mask takes action in an effort to lower the subject's EEG and help the subject relax. In one example, the mask outputs a masking sound, amplifies a masking sound, or alters the spectral output of a masking sound.

In an example, if at 906, the subject is determined to be focused on the sensory output and therefore not have a racing mind, the relaxation mask continues to output the stimulus or a version of the stimulus until a subject is determined to be asleep. In aspects, the mask gradually decreases the sound pressure level of an audio output, slowly decreases the intensity of lights, and decreases haptic outputs when biometric information indicates the subject is asleep. After the subject is determined to be asleep for a predetermined, configurable amount of time, the mask stops outputting, at least, certain stimuli.

The smart relaxation mask uses biometric information from a subject to determine the subject has a racing mind. In response to the determination, the mask adjusts one or more outputs in an effort to shift the subject's focus to the output of the mask and guide the subject to a state of relaxation. This helps the subject relax and fall asleep. The relaxation helps increase a subject's wellness by helping them more consistently fall and stay asleep. The relaxation mask helps treat diagnosable medical conditions, such as insomnia.

In the preceding, reference is made to aspects presented in this disclosure. However, the scope of the present disclosure is not limited to specific described aspects. Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random-access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain or store a program.

The flowchart and block diagrams in the Figures illustrate the architecture, functionality and operation of possible implementations of systems, methods and computer program products according to various aspects. In this regard, each block in the flowchart or block diagrams may represent a module, segment or portion of code, which comprises one or more executable instructions for implementing the specified logical function(s). In some implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

Other Implementations

Figure 10:
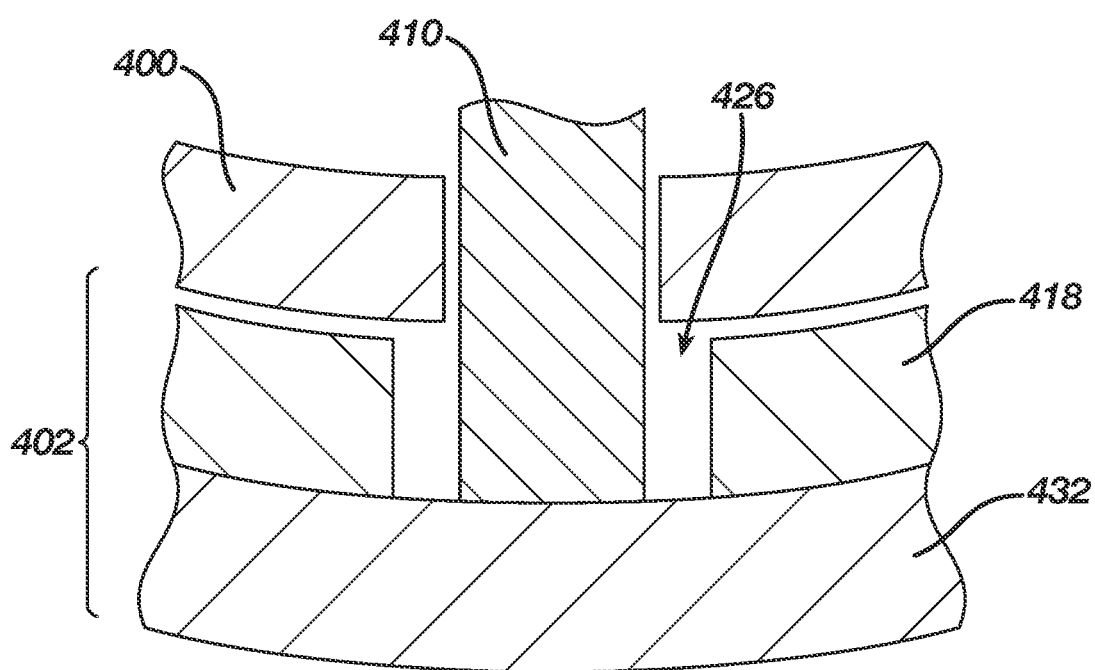
FIG. 10 is a cross-sectional view of an alternative implementation of an earpiece.

While an implementation of an earpiece that makes use of electrically conductive plugs to provide a low impedance electrically conductive path between an eartip and an earbud has been described above, other implementations are possible. For example, FIG. 10 illustrates an alternative implementation in which the first portion 418 of the eartip 402 again defines apertures 426 which are arranged to overlie the pogo pins 410 in the earbud 400, but, unlike the implementation described above, the apertures 426 are not plugged with electrically conductive plugs. Rather, in the implementation illustrated in FIG. 10, the pogo pins 410 (one shown) are allowed to pass through the apertures 426 in the first portion 418 of the eartip 402 to contact the electrically conductive material, e.g., electrically conductive elastomer, e.g., silicone doped with electrically conductive carbon nanoparticles, forming the second portion 432 of the eartip 402. In this implementation, the pogo pin-to-conductive silicone contact may be highly dependent on contact pressure. Accordingly, a contact pressure between the pogo pin 410 and the mating surface on the second portion 432 may need to be higher than what is required for the implementation including the electrically conductive plugs to ensure a good (low impedance) electrical contact. Like reference numbers refer to like elements referenced in other figures described above.

Figure 11:
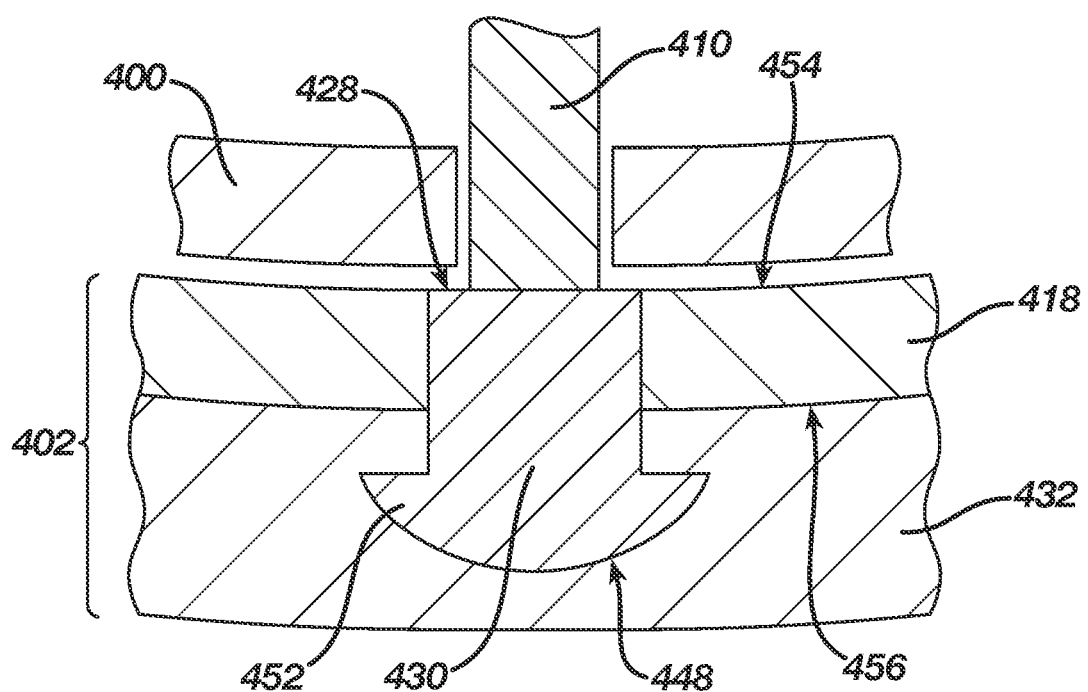
FIG. 11 is a cross-sectional view of yet another implementation of an earpiece.

FIG. 11 illustrates yet another implementation in which the electrically conductive plug 430 is inserted into the aperture 426 formed in the first portion 418 of the eartip 402 such that a portion of the shaft 450 extends outwardly from a second surface 456 of the first portion 418 and such that, during the second molding process, the material that forms the second portion 432 of the eartip 402 covers and wraps around the peripheral edge of the head 454 and contacts the portion of the shaft 450 that protrudes from the first portion 418 of the eartip 402. The second portion 432 is thus bonded to the electrically conductive plugs for electrical contact.

Figure 12A:
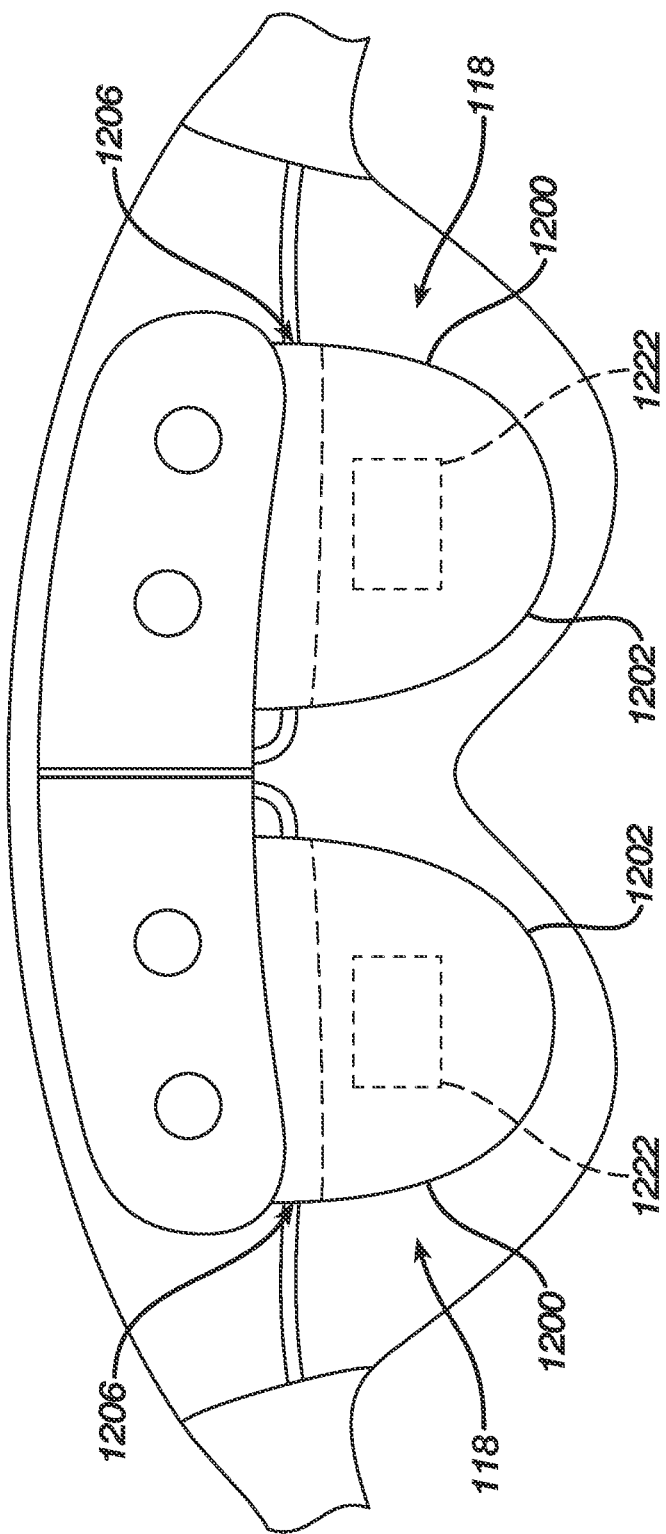
FIG. 12A is a rear view of another implementation of a relaxation mask with discrete light diffusers.

While an implementation of a light diffuser has been described which includes a pair of integral lenses, in some implementations, the relaxation mask may include two discrete light diffusers. For example, in the implementation illustrated in FIGS. 12A &6B, a pair of the light diffusers 1200 (i.e., left and right light diffusers) are disposed in the eye cavities 118 with one light diffuser 1200 in each eye cavity 118. In an example, a light emitting diode (LED) light diffuser outputs light that the subject receives through closed eyelids.

Both of the light diffusers 1200 can have the same construction, so reference made to the light diffuser in the following description is equally applicable to either or both light diffusers. The light diffuser 1200 is formed of silicone and includes a diffusive additive to control opacity. In some cases, the light diffuser 1200 may include between 0% and 30%, e.g., 1% to 30%, e.g., 15%-30%, diffusive additive by volume.

The light diffuser 1200 includes a lens 1202 having the shape of an eye-patch or eyeglass lens (e.g., an "aviator" lens shape). The lens 1202 has a first surface 1204 (FIG. 12B) with a convex curvature that coincides with a concave curvature of the corresponding eye cavity 118.

Figure 12B:
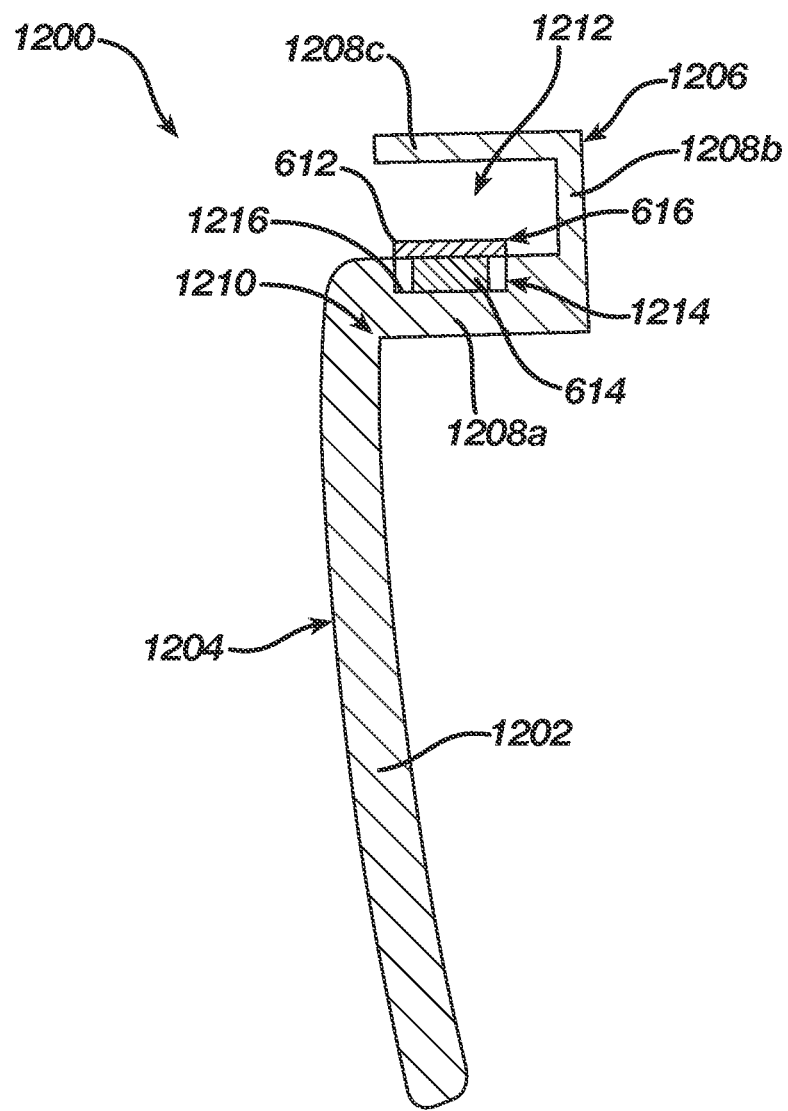
FIG. 12B is a cross-sectional side view of a light diffuser from the relaxation mask of FIG. 12A.

In the implementation illustrated in FIGS. 12A-12D, a coupling member 1206 is formed integrally, e.g., integrally molded, with the lens 1202. A plurality of walls 1208a-c (collectively referenced as "walls 1208") are disposed along a top edge 1210 of the lens 1202 at least partially define a channel 1212. In some cases, the channel 1212 may have a substantially rectangular cross-section. As shown in FIG. 12B, a small recess 1214 is provided in the channel 1212 for receiving the PCB/LED assembly 616, for illuminating the light diffuser 1200. The recess 1214 helps to properly locate the PCB/LED assembly 616 during assemblage. The PCB/LED assembly 616 is held in place within the recess 1214 via a pressure sensitive adhesive 1216. The LED 614 is arranged to fire downward into the top edge 1210 of the light diffuser 1200.

Figure 12C:
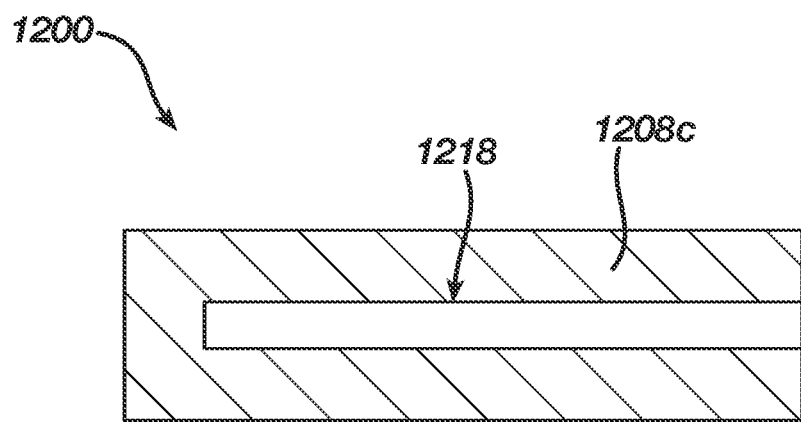
FIG. 12C is a top view of the light diffuser of FIG. 12B.
Figure 12D:
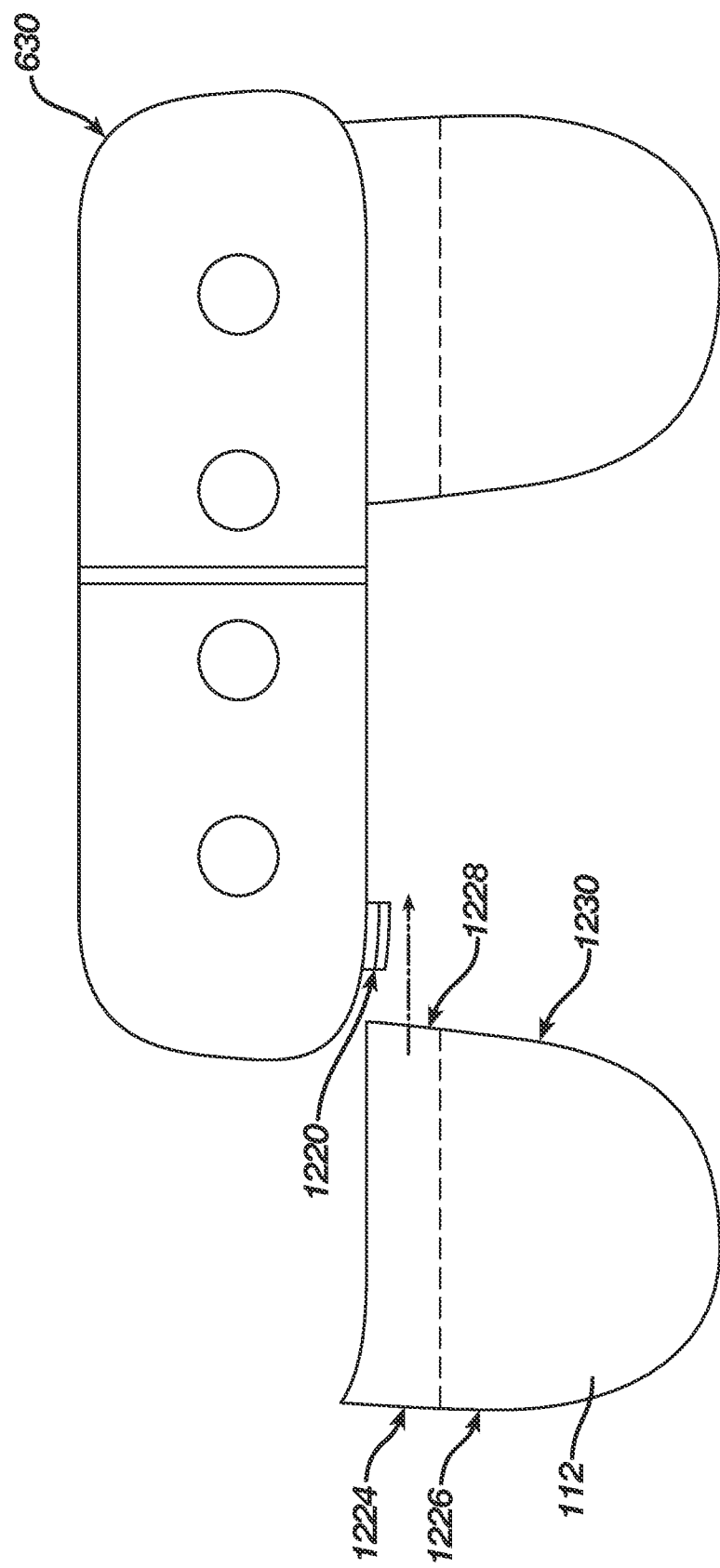
FIG. 12D illustrates the coupling of a light diffuser to an electronics enclosure.

The plurality of walls 1208 includes a bottom wall 1208a that extends along the top edge 1210 of the lens 1200, one or more sidewalls 1208b that extend substantially perpendicular to the bottom wall 1208a, and a top wall 1208c that is substantially parallel with the bottom wall 1208a and spaced therefrom by the sidewall(s) 1208b. The recess 1214 is formed in the bottom wall 1208a. With reference to FIGS. 12C and 12D, the top wall 1208c defines one or more attachment points 1218 for coupling the light diffuser 1200 to the electronics enclosure 630 (FIG. 6A). The one or more attachment points 1218 may include a slot (e.g., a t-shaped slot) that is configured to receive a mating feature 1220 (i.e., a mating attachment point) (FIG. 12D) on the electronics enclosure 630, such as a t-shaped protrusion. A hook-and-loop type fastener 1222 (FIG. 6A), e.g., as sold under the tradename Velcro, may be provided on the first surface 1204 of the light diffuser 1200 to help couple the light diffuser 1200 to the corresponding eye cavity 118 along the inner surface of the mask 102.

The walls 1208 extend from a first open end 1224 of the channel 1212, along a first side edge 1226 of the light diffuser 1200, to a second open end 1228 of the channel 1212, along a second side edge 1230 of the light diffuser 112. In some cases, wiring from the electronics enclosure 630 to the PCB/LED assembly 616, i.e., for powering and controlling the LED 614, is run through one of the open ends 1224, 1228. Alternatively, or additionally, one or more openings may be provided in one or more of the top and sidewalls to accommodate wiring for the PCB/LED assembly 616. The channel 1212 also helps to accommodate the wiring 416 (FIG. 4A) for a corresponding one of the in-ear earpieces 104, 106.

In yet an alternative implementation, the PCB/LED assembly 616 may be disposed along the first surface 1204 of the light diffuser so as to fire directly towards the subject's eye and/or face. In such cases, a more opaque material may be used (e.g., a silicone with a higher concentration of diffusive additive).

While a serpentine wire section is shown and described for providing a spring, in other implementations, the spring may take other forms, such as a coiled wire (retractile cord) section that may be integral with the earpiece wiring. Alternatively, or additionally, a discrete spring may be disposed between the earpiece wiring and the mask for retracting/biasing the wiring and/or earpieces towards the mask.

The invention claimed is:

1. A relaxation face mask comprising:
a main body defining a pair of eye cavities;
the main body positioned in association with the forehead of a subject;
wiring;
an in-ear earpiece coupled to the main body via the wiring;

a spring configured to bias the earpiece towards the main body to retract wire slack into the mask,
wherein the wiring includes a serpentine segment that defines the spring, the serpentine segment positioned longitudinally within the main body;
an electronics enclosure supported by the main body;
wherein a first end of the wiring is coupled to the electronics enclosure and a second end of the wiring is coupled to the earpiece;
wherein the wiring includes a first round section arranged at the first end, a second round section arranged at the second end, and a flat section that extends between the first round section and the second round section; and
wherein the spring is defined by the flat section that includes the serpentine segment.

2. The relaxation mask of claim 1, further comprising: a light diffuser disposed within a first one of the cavities; and a coupling member coupling the light diffuser to the electronics enclosure, wherein the coupling member defines a channel, and wherein the serpentine segment is disposed within the channel.

3. The relaxation mask of claim 1, further comprising a sleeve having a first open end and a second open end, wherein the wiring passes through the sleeve, wherein the sleeve is arranged to overlie a temple region of the subject when the relaxation mask is worn.

4. The relaxation mask of claim 3, wherein a high friction material is disposed on an inner surface of the sleeve and is arranged to inhibit movement of the wiring when the relaxation mask is worn.

5. The relaxation mask of claim 4, wherein the first round section is arranged at an interface with the earpiece, and wherein the flat section extends through the sleeve, wherein the first round section comprises a first portion of a conductive wire surrounded by a first portion of an elastomer having a circular cross-section, and wherein the first flat section comprises a second portion of the conductive wire surrounded by a second portion of the elastomer having a rectangular or elliptical cross- section.

6. The relaxation mask of claim 1, wherein the spring is configured to provide a maximum restoring force of 40 to 60 grams.

7. The relaxation mask of claim 1, further comprising: a light diffuser disposed within a first one of the cavities; and a coupling member coupling the light diffuser to the electronics enclosure, wherein the coupling member defines a channel, and wherein the spring is disposed within the channel.

8. The relaxation mask of claim 1, further comprising: at least one biometric sensor configured to output data associated with the subject wearing the relaxation mask; an electroacoustic transducer supported by the earpiece; a memory coupled to a processor; and instructions stored in the memory that, when executed, cause the processor to: output, via the electroacoustic transducer, an acoustic stimulus; receive the output data from the at least one biometric sensor; correlate the output data and the acoustic stimulus to identify a racing mind state; adjust the acoustic stimulus of the relaxation mask in response to the identified racing mind state;
and output the adjusted acoustic stimulus via the electroacoustic transducer.

9. The relaxation mask of claim 1, wherein the wiring comprises a conductive wire surrounded by an elastomer.

* * * * *